(12) United States Patent
Mendes et al.

(10) Patent No.: US 8,314,218 B2
(45) Date of Patent: Nov. 20, 2012

(54) METHOD OF SYNTHESIZING MACROLIDE COMPOUNDS

(75) Inventors: Zita Mendes, Lisbon (PT); António Carlos Silva Henriques, Forte da Casa (PT); William Heggie, Cabanas (PT)

(73) Assignee: Merial Limited, Duluth, GA (US)

( * ) Notice: Subject to any disclaimer, the term of this patent is extended or adjusted under 35 U.S.C. 154(b) by 276 days.

(21) Appl. No.: 12/604,618

(22) Filed: Oct. 23, 2009

(65) Prior Publication Data

US 2010/0145035 A1 Jun. 10, 2010

Related U.S. Application Data

(60) Provisional application No. 61/108,046, filed on Oct. 24, 2008.

(51) Int. Cl.
*C07H 17/00* (2006.01)
*C07G 3/00* (2006.01)
(52) U.S. Cl. .......................... 536/18.5; 536/7.4
(58) Field of Classification Search .................. None
See application file for complete search history.

(56) References Cited

U.S. PATENT DOCUMENTS

| 5,202,434 A | 4/1993 | Wilkening |
| 5,985,844 A | 11/1999 | Heck et al. |
| 6,013,778 A * | 1/2000 | Heggie et al. ............ 536/7.4 |

FOREIGN PATENT DOCUMENTS

| AU | 2001246636 B2 * | 4/2005 |
| EP | A 0 508 699 A1 | 10/1992 |
| EP | A 0 549 040 A1 | 12/1992 |
| WO | WO 01/72763 A | 10/2001 |

OTHER PUBLICATIONS

Wilkening et al. Tetrahedron, vol. 53, Issue 50, Dec. 15, 1997, pp. 16923-16944.*
Bingwei V. Yang et al. A Novel Product from Beckmann Rearrangement of Erythromycin A 9(E)-oxime. Tetrahedron Letters, vol. 35, No. 19, pp. 3025-3028, 1994.
Slobodan Djokie, et al. Erythromycin Series. Part 11. Ring Expansion of Erythromycin A Oxime by the Beckmann Rearrangement. J. Chem. soc. Perkin Trans. I, 1986.

* cited by examiner

*Primary Examiner* — Layla Bland
(74) *Attorney, Agent, or Firm* — Judy Jarecki-Black; Chad Kitchen; Merial Limited

(57) ABSTRACT

The present invention relates to methods for synthesizing macrolide compounds which are known to have antibacterial activity, and are useful in the therapy of bacterial infections in mammals. More specifically, the invention relates to methods for synthesizing the macrolide antibiotic, gamithromycin utilizing a novel configuration of catalysts, chemical structures, and/or methods. An embodiment of the present invention may include allowing multiple chemical reactions to proceed without the isolation of chemical intermediates. Thus, multiple reactions may occur in one reaction vessel allowing for a considerable decrease in the cycle-time. The present invention also provides a novel method for inhibiting degradation while isolating a structure of a pharmaceutical composition.

15 Claims, 8 Drawing Sheets

METHOD OF SYNTHESIZING MACROLIDE COMPOUNDS

INCORPORATION BY REFERENCE

This application claims the benefit of U.S. Provisional Patent Application No. 61/108,046 filed Oct. 24, 2008, which is incorporated herein by reference in its entirety. The documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to a method for synthesizing a group of chemical compounds having antibacterial activity, which are useful in the therapy of bacterial infections in mammals. More specifically, the invention relates to methods for synthesizing the macrolide compounds, e.g. gamithromycin.

Even more specifically, the invention relates to a method of producing gamithromycin utilizing a novel configuration of catalysts, chemical structures, and/or methods.

The present invention also provides a novel method for inhibiting degradation while isolating a structure of a pharmaceutical composition.

BACKGROUND OF THE INVENTION

Macrolides are a group of chemical compounds, some of which have antibacterial activity and are useful in the therapy of bacterial infections in mammals. Macrolide antibiotics include those having a many-membered lactone ring to which are attached one or more deoxy sugar molecules. These antibiotics are generally bacteriostatic, but have been also been shown to be bacteriocidal to some organisms. Macrolide antibiotics are effective against gram-positive cocci and bacilli, although some of them do possess some activity against some gram-negative organisms. Macrolide antibiotics exert their bacteriostatic activity by inhibiting bacterial protein synthesis. ("Goodman & Gillman's the Pharmacological Basis of Therapeutics," 9th ed., J. G. Hadman & L. E. Limbird, eds., ch. 47, pp. 1135-1140, McGraw-Hill, New York (1996)).

As a class macrolides tend to be colorless and usually crystalline. The compounds are generally stable in near neutral solution, but may be less stable in acid or base solutions. The precursors of macrolide compounds used in the process of the invention (e.g. (9E)-9-deoxy-9-hydroxyiminoerythromycin A (hereinafter "Structure 1"); 9-(Z)-erythromycin oxime (hereinafter "Structure 2"); and 9-Deoxo-12-deoxy-9,12-epoxy-8a,9-didehydro-8a-aza-8a homoerythromycin A (hereinafter "Structure 3") have been described in U.S. Pat. Nos. 5,202,434 and 5,985,844. Furthermore, Yang et al., Tetrahedron Letters, 1994, 35(19), 3025-3028 and Djokic et al., J. Chem. Soc. Perkin Trans. 1, 1986, 1881-1890 describe the synthesis of macrolide compounds that use these compounds as intermediates. However, the synthesis and isolation of macrolide compounds such as gamithromycin typically requires multiple extractions and phase separations.

Therefore, there is still a need for simplifying the synthesis and isolation of macrolides as well as increasing the stability of the macrolides and intermediates thereof.

Citation or identification of any document in this application is not an admission that such document is available as prior art to the present invention.

SUMMARY OF THE INVENTION

The present invention relates to a novel method of synthesizing macrolide compounds. An embodiment of the present invention may include allowing multiple chemical reactions to proceed without the isolation of chemical intermediates. For example, a chemical may be reduced and subsequently alkylated without isolation of the chemical intermediates. Thus, multiple reactions may occur in one reaction vessel which may allow for a considerable decrease in the cycle-time of the process. In an alternate embodiment, one or more of the intermediates may be isolated prior to reaction.

In an embodiment, (9E)-9-deoxy-9-hydroxyiminoerythromycin A (hereinafter "Structure 1") may be isomerized to form 9-(Z)-erythromycin oxime (hereinafter "Structure 2"). In some embodiments, a rearrangement may be used to convert 9-(Z)-erythromycin oxime to 9-deoxo-12-deoxy-9,12-epoxy-8a,9-didehydro-8a-aza-8a homoerythromycin A (hereinafter "Structure 3"). Reduction and alkylation may be used to convert 9-deoxo-12-deoxy-9,12-epoxy-8a,9-didehydro-8a-aza-8a homoerythromycin A to gamithromycin. In another embodiment, the amount of by-products resulting from distillations and washes may be reduced.

Further, an embodiment of the invention may include isolation of an intermediate under conditions which are controlled to inhibit degradation of the intermediate.

These and other embodiments are disclosed or are obvious from and encompassed by the following Detailed Description.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

BRIEF DESCRIPTION OF THE DRAWINGS

The following detailed description, given by way of example, but not intended to limit the invention solely to the specific embodiments described, may best be understood in conjunction with the accompanying drawings, in which.

DETAILED DESCRIPTION

Figure 1:
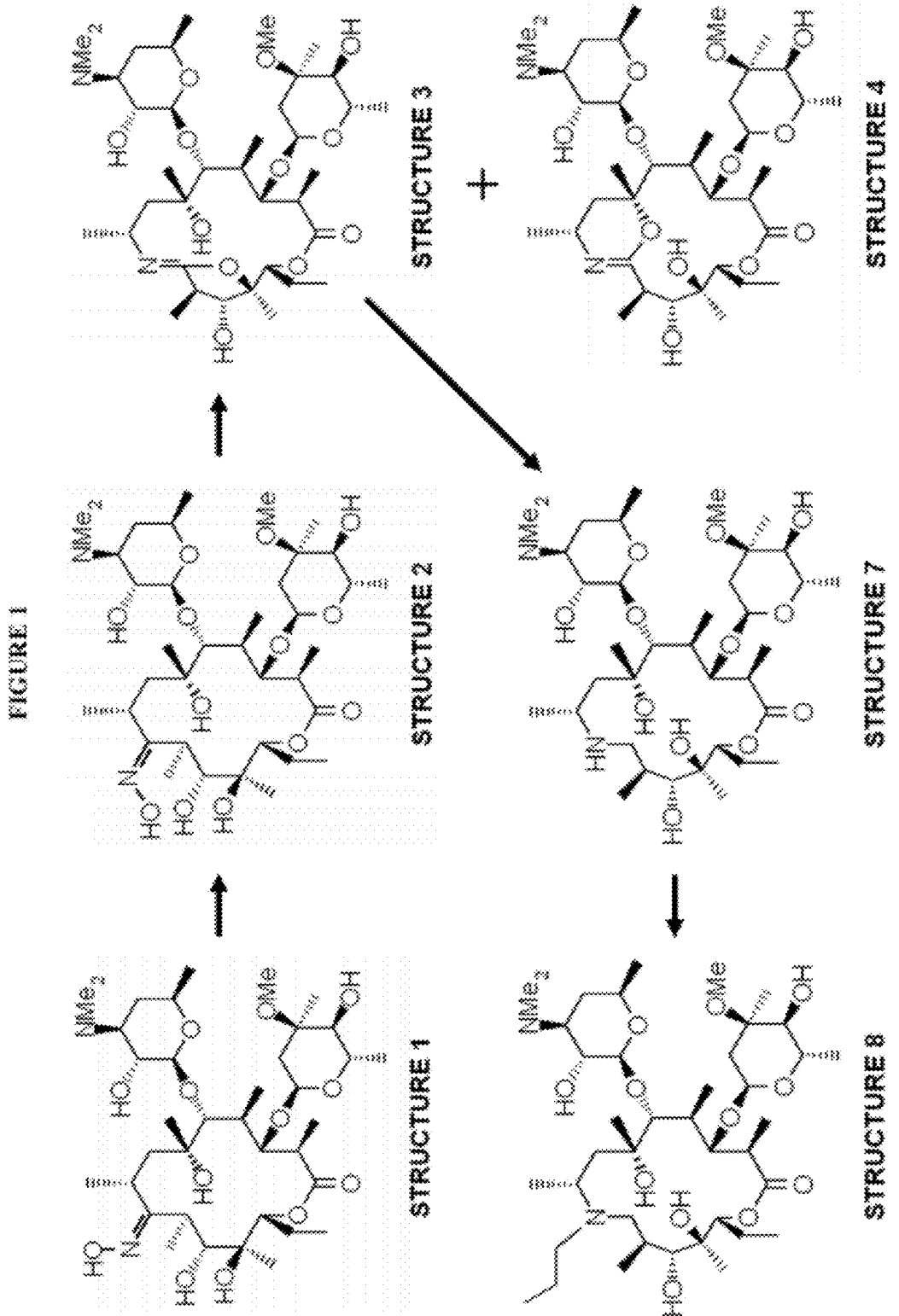
FIG. 1 depicts chemical structures involved in a method for synthesizing gamithromycin.

For clarity, the numbering of the macrocyclic lactones and macrocyclic lactams described herein will use the ring numbering used in U.S. Pat. No. 5,202,434, which is incorporated herein by reference in its entirety. The ring numbering of the erythromycin A lactone ring shown below will be maintained throughout this document for the 14-membered ring compounds described. Similarly, the numbering of the 15-membered lactam described shown below will be used for 15-membered ring compounds described herein.

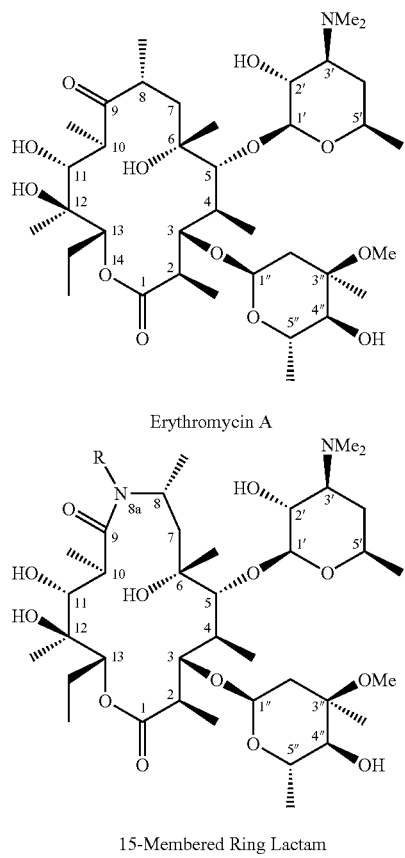

Erythromycin A

15-Membered Ring Lactam

Definitions

Terms used herein will have their customary meaning in the art unless specified otherwise. The organic moieties mentioned in the definitions of the variables of formula (I) or (II) are—like the term halogen—collective terms for individual listings of the individual group members. The prefix $C_n$-$C_m$ indicates in each case the possible number of carbon atoms in the group.

The term "alkyl" as used herein, refers to saturated straight, branched, cyclic, primary, secondary or tertiary hydrocarbons, including those having 1 to 20 atoms. In some embodiments, alkyl groups will include $C_1$-$C_{12}$, $C_1$-$C_{10}$, $C_1$-$C_8$, $C_1$-$C_6$ or $C_1$-$C_4$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "alkenyl" refers to both straight and branched carbon chains which have at least one carbon-carbon double bond. In some embodiments, alkenyl groups may include $C_2$-$C_{20}$ alkenyl groups. In other embodiments, alkenyl includes $C_2$-$C_{12}$, $C_2$-$C_{10}$, $C_2$-$C_8$, $C_2$-$C_6$ or $C_2$-$C_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Alkynyl" refers to both straight and branched carbon chains which have at least one carbon-carbon triple bond. In one embodiment of alkynyl, the number of triple bonds is 1-3; in another embodiment of alkynyl, the number of triple bonds is one or two. In some embodiments, alkynyl groups include from $C_2$-$C_{20}$ alkynyl groups. In other embodiments, alkynyl groups may include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

"Aryl" refers to a monovalent aromatic carbocyclic group of from 6 to 14 carbon atoms having a single ring or multiple condensed rings. In some embodiments, aryl groups include $C_6$-$C_{10}$ aryl groups. Aryl groups include, but are not limited to, phenyl, biphenyl, naphthyl, tetrahydronaphtyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylamino, alkenylamino, alkynylamino, di(alkyl)amino, di(alkenyl)-amino, di(alkynyl)amino, or trialkylsilyl.

The term "aralkyl" refers to an aryl group that is bonded to the parent compound through a diradical alkylene bridge, ($-CH_2-$)$_n$, where n is 1-12 and where "aryl" is as defined above.

"Heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple condensed rings provided that the point of attachment is through a heteroaryl ring atom. Preferred heteroaryls include pyridyl, piridazinyl, pyrimidinyl, pyrazinyl, triazinyl, pyrrolyl, indolyl, quinolinyl, isoquinolinyl, quinazolinyl, quinoxalinyl, furanyl, thiophenyl, furyl, pyrrolyl, imidazolyl, oxazolyl, isoxazolyl, isothiazolyl, pyrazolyl benzofuranyl, and benzothiophenyl. Heteroaryl rings may be unsubstituted or substituted by one or more moieties as described for aryl above.

In some embodiments, the invention may include the pharmaceutically acceptable or veterinarily acceptable salts of the compounds shown in FIG. 1. Such salts are generally prepared as acid addition salts by combining a macrolide compound with one to three equivalents of an appropriate acid in an inert solvent. The salt is recovered by solvent evaporation or by filtration if the salt precipitates spontaneously, or by precipitation using a co-solvent or a non-polar co-solvent followed by filtration. Salts may include, but are not limited to, acetate, benzenesulfonate, benzoate, bicarbonate, bisulfate, bitartrate, borate, bromide, calcium, calcium edetate, edentate, camsylate, carbonate, chloride, clavulanate, citrate, dihydrochloride, edentate, edisylate, estolate, esylate, ethylsuccinate, fumarate, gluceptate, glucoheptonate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phosphate/diphosphate, polygalacturonate, salicylate, stearate, subacetate, succinate, tannate, tartrate, teoclate, tosylate, triethiodode, valerate and/or combinations thereof.

In one embodiment, Structure 1 may be isomerized to form Structure 2 as shown in FIG. 1. In some embodiments, the isomerization may be carried in the presence of one or more reagents. Suitable reagents include, but are not limited to, solvents and bases. Suitable solvents for the transformation may be common protic or aprotic solvents known in the art. The following list of reagents below is illustrative, and it will be clear to one of skill in the art that other bases and solvents known or yet to be discovered in the art should not be excluded.

Suitable bases include, but are not limited to, hydroxides including, but not limited to, lithium hydroxide, sodium hydroxide, potassium hydroxide, cesium hydroxide, calcium hydroxide, magnesium hydroxide, tetramethylammonium hydroxide, benzyltrimethylammonium hydroxide, tetraethylammonium hydroxide, tetrabutylammonium hydroxide and the like; alkoxides including, but not limited to, lithium methoxide, lithium ethoxide, lithium isopropoxide, lithium n-butoxide, lithium sec-butoxide, sodium methoxide, sodium ethoxide, sodium n-propoxide, sodium iso-propoxide, sodium n-butoxide, sodium sec-butoxide, sodium tert-butoxide, sodium trimethylsilanoate, potassium methoxide, potassium ethoxide, potassium tert-butoxide, potassium trimethylsilanoate, potassium sec-butoxide, cesium tert-butoxide, calcium methoxide, magnesium ethoxide, titanium (IV) ethoxide, titanium (IV) isopropoxide, benzyltrimethylammonium methoxide, and the like; carbonates including, but not limited to, potassium carbonate, cesium carbonate, sodium carbonate, and the like; amides including, but not limited to, lithium amide, lithium dimethylamide, lithium diisopropylamide, lithium dicyclohexylamide, lithium bis(trimethylsilyl) amide, sodium amide potassium bis(trimethylsilyl) amide, and the like, amines including, but not limited to, 1,1,3,3-tetramethyl guanidine, 1,8-diazabicyclo[5,4,0]-undec-7-ene, 1,8-bis(dimethylamino)-naphthalene), and the like, and hydrides including, but not limited to, lithium hydride, sodium hydride, potassium hydride, and the like.

Suitable solvents include those solvents miscible with water as well as those that are not miscible with water. In some embodiments, suitable solvents include, but are not limited to, water, methanol, ethanol, isopropanol, normal-butanol, sec-butanol, tert-butanol, diethyl ether, tetrahydrofuran, dimethoxyethane, toluene, dichloromethane, chloroform, dimethylformamide, dimethylacetamide, 1,3-dimethyl-2-imidazolidinone, 1-ethyl-2-pyrrolidinone, 1-methyl-2-pyrrolidinone, hexamethylphosphoramide, nitromethane, acetonitrile, dioxane, pyridine, dimethyl sulfoxide, and the like, and/or combinations thereof.

In one embodiment, Structure 1 may react with a base in the presence of a solvent to form Structure 2. In one embodiment, the base may be lithium hydroxide and the solvent may be ethanol. In certain embodiments, hydrates of the base, such as the monohydrate of lithium hydroxide, are used.

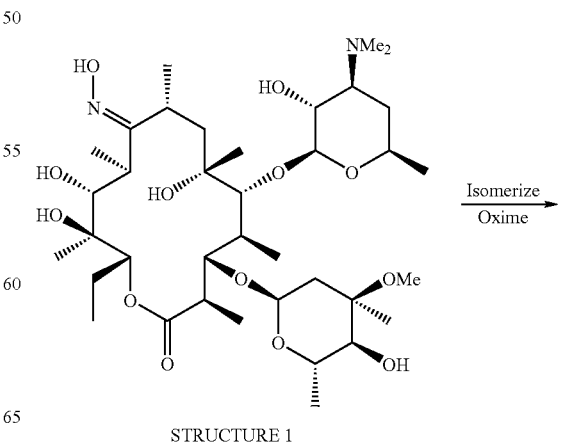

STRUCTURE 1

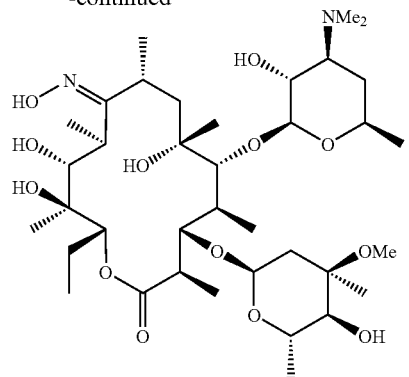

STRUCTURE 2

In some embodiments, optimization of the method of the isomerization may include use of a base and solvent combination sufficient to substantially deprotonate the hydroxy-imino group (oxime) of Structure 1. In one embodiment, reaction conditions may be controlled to stabilize the oxime anion for the time period necessary to complete the isomerization process.

In another embodiment, an equilibrium condition may be created upon addition of the base to Structure 1. One embodiment may include protonation of oxime anions to give the neutral oxime product mixture from which Structure 2 may be isolated by crystallization, by chromatography followed by crystallization, or by crystallization followed by chromatography. The relative amounts of Structure 1 and Structure 2 in the equilibrium mixture may be controlled by a number of factors. These factors may include, but are not limited to, the strength and quantity of the base reagent, the size and polarizability of the counterion, the reaction solvent, and/or the reaction temperature.

In some embodiments, the isomerization reaction may be carried out at a concentration of about 1% to about 25% weight of Structure 1/volume of solvent. In other embodiments, the concentration of Structure 1 may be about 5% to about 25%, about 5% to about 15%, or about 7% to about 12% by weight of Structure 1/volume of solvent. In a preferred embodiment, the weight of Structure 1/volume of solvent may be about 10%.

In some embodiments, the amount of base used may be in a range from about 1 to about 10 molar equivalents based on the amount of starting Structure 1. In other embodiments, the amount of base may be in a range from about 1 to about 3 molar equivalents. In one preferred embodiment, the process may include using an amount of base having a value of about 2 molar equivalents.

In some embodiments the reaction temperature may be monitored. In an embodiment, conditions of the reaction may be controlled to maintain a temperature within a range from about −10° C. to about 80° C., or from about 0° C. to about 80° C. The temperature may be maintained in a range from about 10° C. to about 70° C. in one embodiment. In another embodiment, a reaction temperature may be maintained within a range from about 15° C. to about 60° C. Another embodiment may include maintaining a reaction temperature within a range from about 20° C. to about 50° C. In still another embodiment, the reaction temperature may be maintained in a range from about 20° C. to about 30° C. Some embodiments may include maintaining a temperature within a range from about 22° C. to about 25° C.

In some embodiments, the reaction time may vary. For example, the reaction may be allowed to run for about 0.5 hours to about 20 days. Another embodiment may include allowing the reaction to run for about 1 hour to about 15 days. In other embodiments, the reaction time may be within a range from about 3 hours to about 5 days. Alternately, a reaction time may be within a range from about 6 hours to about 24 hours in one embodiment. Further, one embodiment may include a reaction time of about 10 hours to about 24 hours. In another embodiment, a reaction time may be within a range from about 20 hours to about 24 hours.

Equilibrium in these reactions may be influenced by a number of factors including, but not limited to, strength and quantity of the base, the size and polarization of a counterion, the reaction solvent, and/or the reaction temperature. Any solvent or base known or yet to be discovered in the art may be used.

One embodiment of the invention may include isolating Structure 2 by any suitable means. For example, in one embodiment, Structure 2 may be isolated using crystallization. In other embodiments, isolation of Structure 2 may include use of chromatography followed by crystallization, or crystallization followed by chromatography. It will be apparent to one of skill in the art that Structure 2 or any other compound of the invention may be crystallized from solution by any method that suitably reduces the solubility of the compound in the solvent. Crystallization methods may include, but are not limited to, reducing the temperature of a solution, addition of an anti-solvent in which the compound is not soluble, formation of an insoluble salt, and the like.

The process utilizes a rearrangement to form a mixture of Structure 3 and Structure 5 from an oxime of Structure 1 or Structure 2. The Beckmann rearrangement of ketoximes (see for example, "Comprehensive Organic Chemistry," I. O. Sutherland (Ed.),

STRUCTURE 3

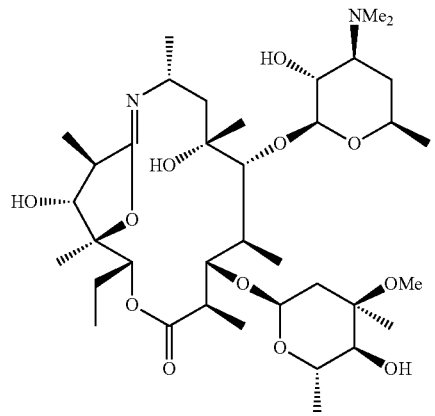

STRUCTURE 4

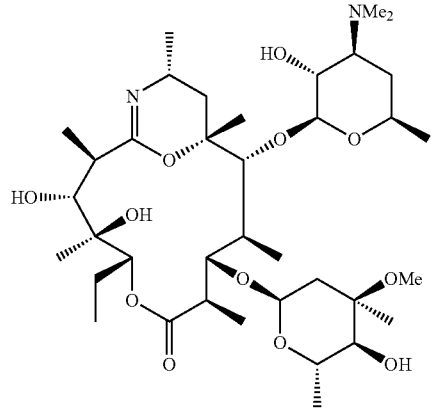

Pergamon Press, New York, 1979, Vol. 2, pgs. 398-400 and 967-968; and Gawley, *Organic Reactions*, 1988, 35, 1-420) may lead to carboxamides and, in cyclic systems, to ring expanded lactams. In an embodiment, an acid-catalyzed rearrangement, such as a Beckmann rearrangement, may be utilized to form a mixture from Structure 2. For example, in certain embodiments of the invention, a mixture resulting from a Beckmann rearrangement of Structure 2 may include, but is not limited to 9-deoxo-12-deoxy-9,12-epoxy-8a,9-didehydro-8a-aza-8a homoerythromycin A (hereinafter "Structure 3") and/or 9-deoxo-6-deoxy-6,9-epoxy-8a,9-didehydro-8a-aza-8a homoerythromycin A (hereinafter "Structure 4").

Although not wishing to be bound by theory, in an embodiment, the mechanism of the Beckmann rearrangement may involve an initial conversion of the oxime hydroxyl group to a leaving group which is then lost with concomitant migration of the oxime carbon substituent that is situated anti to the leaving group. In aqueous media, an intermediate nitrilium cation thus formed usually reacts with water to afford the amide product. The nitrilium intermediate may be trapped by other suitable nucleophiles thereby leading to imino products, such as imidates and amidines.

The Beckmann rearrangement may be performed in varying conditions including, but not limited to, acidic, basic and neutral conditions. An embodiment may include controlling reaction conditions and/or reagents to give varying proportions of products. Common acidic reagents which may be utilized include, but are not limited to, sulfuric acid including concentrated sulfuric acid, polyphosphoric acid, thionyl chloride, phosphorous pentachloride, sulfur dioxide, formic acid and/or combinations thereof. In some embodiments, a Beckmann rearrangement may occur by heating the oxime with silica gel in a suitable solvent. Suitable solvents include, but are not limited to, aromatic solvents such as toluene or xylene. An alternate embodiment of a Beckmann rearrangement may include heating the oxime under mildly basic conditions in a suitable solvent, including hexamethylphosphoramide.

In one embodiment, a Beckmann rearrangement may include initial O-sulfonylation of the oxime group with a suitable sulfonylating agent. Sulfonylating agents are well known in the art and include, but are not limited to, an alkylsulfonyl halide, arylsulfonyl halide or arylsulfonic anhydride. An intermediate oxime sulfonate formed this way may be isolated or may be converted in situ to the rearranged products. Sulfonylation and rearrangement reactions may be performed in the presence of an organic or inorganic base.

Some embodiments may include sulfonylating reagents for effecting the rearrangement of Structure 2 including, but not limited to, methanesulfonyl chloride, benzenesulfonyl chloride, 4-acetamidobenzenesulfonyl chloride, p-toluenesulfonyl chloride, benzenesulfonic anhydride, p-toluenesulfonic anhydride and/or other sulfonylating reagents known or yet to be discovered in the art. The reaction may be carried out in the presence of an inorganic base including, but not limited to, sodium bicarbonate or potassium carbonate. Alternately, in some embodiments the reaction may occur in the presence of an organic base including, but not limited to, pyridine, 4-dimethylaminopyridine, triethylamine, N,N-diisopropylethylamine, and/or any organic base known or yet to be discovered in the art. Suitable solvents may include, but are not limited to, aqueous mixtures such as aqueous acetone or aqueous dioxane and organic solvents such as dichloromethane, chloroform, ethyl acetate, diethyl ether, tetrahydrofuran, toluene, acetonitrile, pyridine, and the like. In addition, mixtures of organic solvents, especially those containing pyridine, may be used. In an embodiment, the reaction may be performed using about one to about three molar equivalents of the sulfonylating agent and about one or more molar equivalents of base at a reaction temperature of about −20° C. to about 50° C. In one embodiment, pyridine may be used as both solvent and base.

In an embodiment, a distribution of products resulting from a Beckmann rearrangement of Structure 2 may depend on the particular reaction conditions employed. For example, when the rearrangement is effected with p-toluenesulfonyl chloride and sodium bicarbonate in aqueous acetone, the major products may include a lactam and Structure 4. In an embodiment, a Beckmann rearrangement of Structure 2 under anhydrous conditions leads to a product mixture comprising the 9,12- and 6,9-bridged iminoethers, Structure 3 and Structure 4. For example, when the reaction is conducted under anhydrous conditions, such as p-toluenesulfonyl chloride in pyridine, the major products may include Structure 3 and Structure 4. The ratio of products may be affected by the addition of co-solvents, temperature, and/or the initial oxime concentration. For example, increasing a proportion of pyridine as solvent, increasing the reaction temperature, and/or decreasing the initial oxime concentration may favor the formation of Structure 3 over Structure 4.

In one embodiment, a Beckmann rearrangement of Structure 2 may involve the addition of a solution of about 2.5 molar equivalents of p-toluenesulfonyl chloride in diethyl ether to a solution of Structure 2 in pyridine at a temperature in a range from about 0° C. to about 5° C. One embodiment may include oxime O-sulfonylation and subsequent rearrangement under the reaction conditions to form a mixture of Structure 3 and Structure 4.

An embodiment of the invention may include purifying products after the Beckmann rearrangement of Structure 2. For example, chromatographic methods including, but not limited to, column chromatography on silica gel or reverse phase, high-pressure liquid chromatography may be used, among other chromatographic methods. Structure 3 and Structure 4 may be separated by chromatographic methods. In another embodiment, Structure 3 may be purified by crystallization. In another embodiment, the product may be purified by a combination of crystallization and chromatography.

In some embodiments, the mixture of Structure 3 and Structure 4 may be reacted further without purification or with limited purification. In an embodiment, further reactions may be allowed to occur without isolating individual structures. For example, the mixture of isomers may be reduced without purification.

Figure 2:
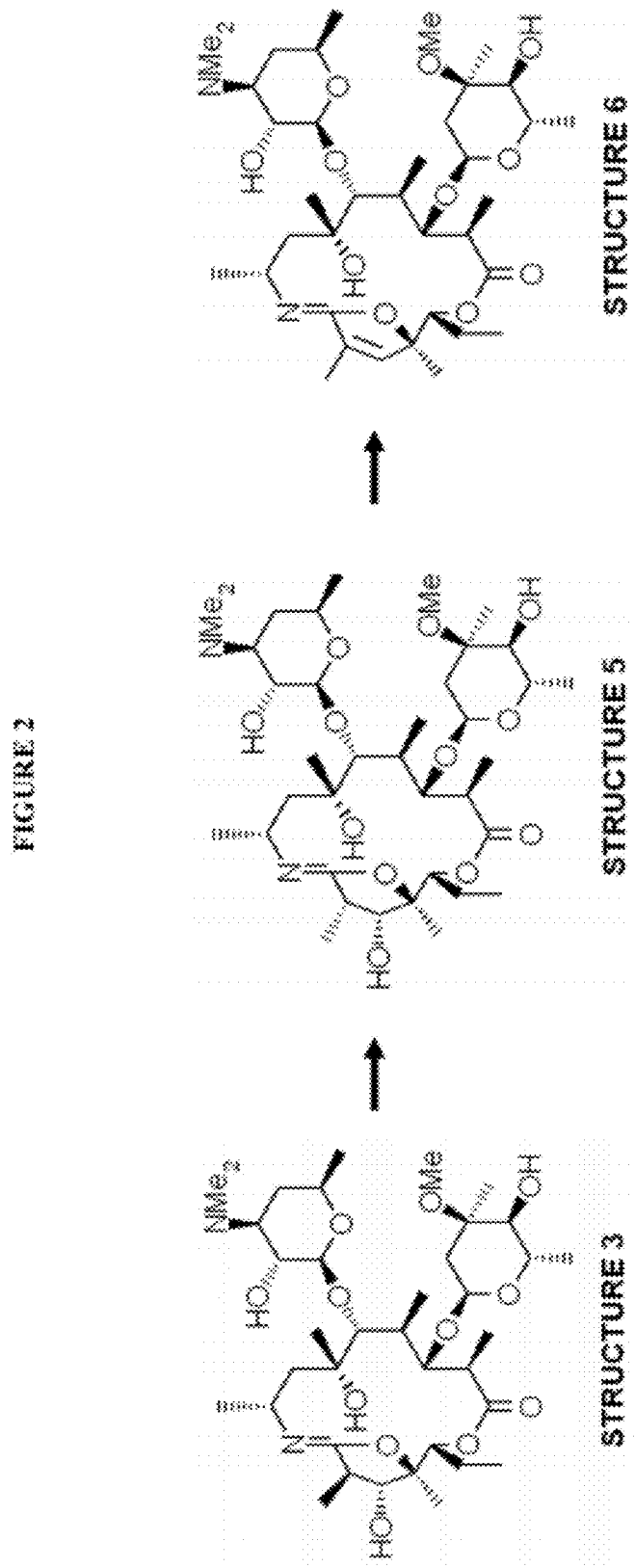
FIG. 2 depicts chemical structures of degradants of Structure 3 in a method for synthesizing gamithromycin.

In one embodiment, Structure 3 may be isolated from the mixture using a low temperature purification procedure. For example, in one embodiment isolation of Structure 3 in dichloromethane may be carried out at a temperature between about −20° C. to about 15° C. More typically, the isolation may be carried out at a temperature of about −20° C. to about 10° C., about −10° C. to about 5° C., about −5° C. to about 5° C., or preferably about 0° C. to about 5° C. In another embodiment, the purification may be conducted below about 25° C., below about 20° C., or below about 15° C. In some embodiments, use of a low temperature purification procedure may inhibit degradation of Structure 3 to degradation products including, but not limited to Structure 5 and/or Structure 6 as depicted in FIG. 2. In an embodiment, degradation of Structure 3 may be inhibited by removal of p-toluenesulfonic acid (hereinafter "PTSA") from the dichloromethane phase. Some embodiments may include removing solvents from the combined organic phases under vacuum at a temperature below 35° C. An embodiment may include removing components, such as dichloromethane, with methyl tertiary butyl ether (hereinafter "MTBE") by concentrating 1 or 2 times to a residue.

In an embodiment, Structure 3 may be formed by internal trapping of the intermediate nitrilium species by the hydroxyl group at C-12. Structure 3 may be isolated as a mixture of major and minor forms that are isomeric about the imino double bond. In an embodiment, the initial mixture of isomers may equilibrate at room temperature, both in solution or on storing as a crude product, to approximately a 1:1 mixture of isomers. In one embodiment, the first-formed, major isomer may be isolated from the mixture by crystallization from solution in a suitable solvent, such as a nitromethane solution.

In an embodiment, both forms of the isomer (i.e., Structure 3 and Structure 4) may easily be reduced to 9-deoxo-8a-aza-8a-homoerythromycin A (hereinafter "Structure 7").

An embodiment may include a wash of the reaction mixture. In one embodiment, the wash may be done with a suitable organic solvent. Suitable organic solvents that may be used for the wash are well known in the art and include, but are not limited to, hydrocarbon solvents such as heptane, hexane, pentane, and the like. Other organic solvents include ethers such as MTBE and the like, alkyl esters such as ethyl acetate and the like, aromatic solvents such as toluene, or others. A heptane wash may remove some pyridine in the reaction mixture. In an embodiment, the resulting oil may be diluted with a second solvent mixture, such as dichloromethane and water. In an alternate embodiment, the resulting oil may be washed with 1,3-dimethyl-2-imidazolidinone or N,N'-dimethylethyleneurea (hereinafter "DMEU"). In some embodiments, the pH of the mixture may be adjusted to a value in a range from about 7 to about 12. Further some embodiments may include adjusting the pH to a value in a range from about 9 to about 10. The pH adjustment may be made using any pH modifier known in the art including, but not limited to, metal hydroxides such as aqueous sodium hydroxide, lithium hydroxide or potassium hydroxide solution. Other suitable pH adjusters include carbonate and bicarbonate salts, and amines. An embodiment may include a phase separation. Further, some embodiments may include a back wash of the aqueous phase using dichloromethane, or another suitable water immiscible solvent.

In an embodiment, pyridine in the residue may be removed during crystallization from MTBE. An embodiment may include crystallizing the product at room temperature and then cooling it to temperature within a range about −20° C. to about 15° C. or more typically about −20° C. to about 10° C. In other embodiments, the mixture is cooled to about −10° C. to about 10° C., about −5° C. to about 10° C., or about 0° C. to about 5° C. In some embodiments, the resulting material may be stirred at this temperature for a period of time to increase yield. For example, a material may be stirred for an hour or more to increase yield.

In an embodiment, Structure 3 may be isolated after filtration and a low temperature MBTE wash of the resulting yellow cake. Other chemical structures including, but not limited to Structure 4 and degradation products (e.g., Structure 5 and Structure 6—see FIG. 2) may remain dissolved in the mother-liquors after the rearrangement reaction. In an embodiment, Structure 3 may be stored in a solid form. Storage in a solid form may inhibit degradation.

In some embodiments, Structure 7 may be synthesized by reduction of Structure 3 with a suitable reducing agent. Various reagents that reduce iminoethers, including those of Structure 3 and 4, to the corresponding amines are known in the art (see for example "The Chemistry of Amidines and Imidates," S. Patai (Ed.), John Wiley and Sons, 1975, pgs. 460-461 and "Comprehensive Organic Chemistry," I. O. Sutherland (Ed.), Pergamon Press, New York, 1979, Vol. 2, pg. 495). In this regard, U.S. Pat. No. 5,985,844 describes that the reduction of cyclic imino ethers is preferably conducted with metal hydride reagents, including sodium borohydride and derivatives. However, it has been found that reduction imino ethers of Structure 3 and 4 with metal hydride reagents, including borohydride reagents, results in boron salts that complicate the isolation of the product and lead to lower yields and purity.

Therefore, in one embodiment of the invention, Structure 7 is formed by the reduction of Structure 3 using hydrogenation under conditions that provides superior quality and yield of the products. The improved hydrogenation reaction of the invention allows for a one-pot conversion of Structure 3 to a macrocycle of Structure 8 in certain embodiments. In an embodiment, Structure 7 may be formed from the mixture resulting after the rearrangement. For example, the mixture resulting from the Beckmann rearrangement of Structure 2 may be hydrogenated to form Structure 7 with a suitable pressure of hydrogen. Some embodiments may include the use of a catalyst during hydrogenation. Catalysts may include, but are not limited to, noble metals and their oxidized forms (e.g., platinum oxide), palladium based catalysts (e.g., palladium on carbon, palladium hydroxide on carbon) platinum based catalysts (e.g., platinum on carbon), rhodium based catalysts (e.g., rhodium on carbon), iridium based catalysts, ruthenium based catalysts, and/or any catalyst known or yet to be discovered in the art. In some embodiments, catalysts may be homogeneous or heterogeneous.

In an embodiment, conditions may be controlled to enhance formation of Structure 7. For example, an embodiment may include operating at room temperature, and at a hydrogen pressure of 50 bar.

In an embodiment, the hydrogenation reaction used to form Structure 7 may utilize a solvent including, but not limited to, acetic acid, formamide, acetamide, 2-pyrrolidone; polar aprotic solvents including, but not limited to, DMEU, dimethylacetamide (hereinafter "DMA"), diethylacetamide, dimethyl sulfoxide (hereinafter "DMSO"), dimethylformamide (hereinafter "DMF"), N-methylpyrrolidone ("NMP"), dioxane, tetrahydrofuran, esters such as ethyl acetate, nitriles such as acetonitrile, and hexamethylphosphorotriamide and/or other solvents known or yet to be discovered in the art.

In some embodiments, hydrogenation reactions may be carried out at a temperature in a range between about −20° C. to about 40° C. In other embodiments, the hydrogenation reaction may be conducted at a temperature of about −20° C. to about 30° C., or more typically about −20° C. to about 20° C. Preferably, the reaction is carried out at a temperature of about −10° C. to about 20° C., about −5° C. to about 20° C., about −5° C. to about 15° C., or about 5° C. to about 20° C. Controlling a temperature of the reaction may inhibit the formation of degradation products in some embodiments.

In one embodiment, Structure 7 may be synthesized directly from Structure 2. A polar aprotic solvent may be added to a mixture in the presence of a catalyst. For example, DMA may be added to Structure 7 in the presence of catalyst having 50% by weight of platinum on carbon. In some embodiments, structure 2 may be isolated from a mixture prior to the reaction. An embodiment may include reacting a mixture including Structure 2 to form Structure 7. In one embodiment, conditions in the mixture may be controlled. For example, the mixture may be stirred while maintaining a temperature of about 15° C. and a hydrogen pressure of about 50 bar.

As shown in FIG. 1 gamithromycin (hereinafter "Structure 8 (Gamithromycin)") may be formed by reductive amination of Structure 7 in the presence of propanal and a suitable reducing agent. In one embodiment, the reductive amination reaction is carried out in the presence of hydrogen under pressure. In another embodiment, the reductive amination reaction may be carried out in the presence of a hydride reducing agent including, but not limited to a boron-based hydride reducing agent such as sodium cyanoborohydride, and the like. In another embodiment of the invention, compound of Structure 8a, wherein R is hydrogen, alkyl, alkenyl, alkynyl, aryl, heteroaryl or aralkyl. In one embodiment, a compound where R is $C_1$-$C_{10}$ alkyl can be obtained by using the appropriate alkylating agent.

(Sturcture 8a)

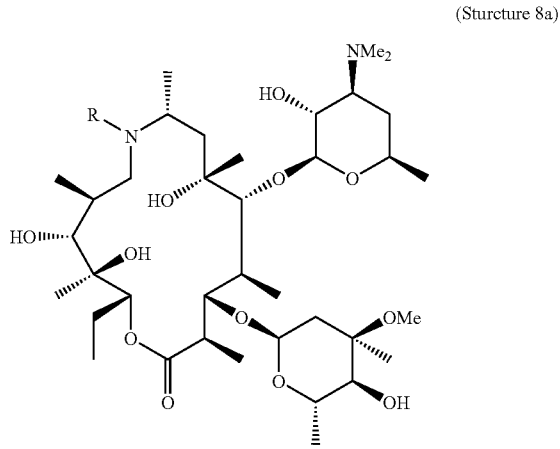

In yet another embodiment of the invention, R is $C_1$-$C_4$ alkyl.

In one embodiment of the invention, the reaction may occur using a catalyst. For example, a palladium catalyst or a platinum catalyst may be used. In an embodiment, a complete reaction may occur within a few hours when using propanal in excess. Thus, utilizing propanal as both a reagent and solvent may decrease reaction time.

In an embodiment, pH may be controlled within a range from about 5.0 to about 5.5 during the reactions. One embodiment may include controlling a pH of a reaction mixture within a range from about 4.5 to about 5.5. Preferably, the pH is controlled at about 5.0 to about 5.5 prior to hydrogenation. In an embodiment, adjustments to pH may be made using acetic acid.

An embodiment may include maintaining a temperature of the reaction mixture in a range from about 20° C. to about 60° C., about 30° C. to about 50° C., or about 40° C. to about 50° C. Preferably, the temperature is about 40° C. to about 45° C.

In an embodiment, Structure 8 (Gamithromycin) may be synthesized from Structure 3 without isolating the Structure 7 intermediate. Since the reductive amination may use a catalyst similar to the catalyst used in the synthesis of Structure 7, these steps may be combined in some embodiments. Thus, one embodiment may include forming Structure 8 (Gamithromycin) without isolating the Structure 7 intermediate. In an embodiment, Structure 7 and Structure 8 (Gamithromycin) intermediates may be synthesized in a single reaction vessel without isolation. In an embodiment, this may decrease cycle time.

The invention will now be further described by way of the following non-limiting examples.

EXAMPLES

The gamithromycin was manufactured as outlined in FIG. 1. Initially the goal was to prepare Structure 7 without the isolation of the intermediate, Structure 3. This would have maintained the same number of isolated intermediates as in the presently used process. However, the chemical instability of the Imidate-4 intermediate (Structure 3) in varying conditions resulted in degradation. The degradation products included Structure 5 and Structure 6. Varying conditions included low pH and some solvent solutions. Attempts were made to isolate Imidate-4 as a stable solid before carrying out the subsequent steps.

Example 1

Formation of Structure 3

A compound of Structure 2 (30 g) was mixed with pyridine (219.4 ml) and cooled to between 2° C. and 6° C. A solution of 4-toluenesulfonyl chloride (hereinafter "p-TsCl") (16.5 g) in methyl t-butyl ether (64.4 ml) was added and the resulting solution was stirred for about 4 hours at between 2° C. and 6° C. and was then cooled to between −15° C. and −10° C.

Heptane (282 ml) was precooled to less than −10° C. and was added to the solution with stirring. After stirring, the phases were allowed to separate for at least 40 minutes. The upper phase (heptane phase) was removed and dichloromethane (403 ml) and water (503 ml) were added to the aqueous phase maintaining the temperature at between 0° C. and 5° C. The pH was adjusted to between 9 and 10 with sodium hydroxide solution and the mixture was stirred for at least 40 minutes at between 0° C. and 5° C. The aqueous phase was removed and backwashed twice with dichloromethane (60 ml). The combined organic phases were dried with sodium sulfate and the dried filtrate was concentrated to the residue at a temperature below 35° C. under vacuum. Methyl t-butyl ether (MTBE) and absolute ethanol were added and the mixture was concentrated to the residue again. The obtained solid was suspended in MTBE and stirred for 4 hours before cooling to between 0° C. and 5° C. The suspension was stirred for at least 1 hour before filtration and washed with MTBE (2 times with 30 ml) previously cooled to between 0° C. and 5° C. The wet solid was dried to afford a pale yellow solid (19.26 g) of Structure 3.

Example 2

Formation of Structure 7

A compound of Structure 3 (8 g) in DMA (80 ml) with catalyst Pt/$C_5$% (4.0 g) was stirred at between 15° C. between 25° C. with a hydrogen pressure of 50 bar. Acetic acid addition (0.5 ml) was necessary to achieve reaction completion. Water (80 ml) was added to the suspension and the suspension was filtered through a cellulose bed. The filter cake was washed with water (80 ml) and to the resulting filtrate was added dichloromethane (160 ml) and the biphasic mixture was stirred for at least 1 hour. The organic phase was removed and dichloromethane (160 ml) was added to the aqueous phase prior to pH adjustment to between 9 and 11 with sodium hydroxide solution. The biphasic mixture was stirred and the separated organic phase containing Structure 7 was washed with water (160 ml). The obtained organic phase was dried with sodium sulfate and the dried solution was concentrated to the residue at a temperature below 50° C. under vacuum to afford an oil of Structure 7 (13.84 g).

Example 3

Formation of Structure 8 (Gamithromycin)

To the oily residue of Structure 7 (13.84 g) were added propanal (80 ml), Pd/C 3% (8.0 g) catalyst and acetic acid (7.5 ml). The suspension was stirred at a temperature between 40° C. and 45° C. with a hydrogen pressure of about 20 bar for at least 4 hours. Water (80 ml) was added to the suspension and the suspension was filtered through a cellulose bed. The filter cake was washed with water (80 ml) and to the resulting filtrate was added MTBE (160 ml) and the biphasic mixture was stirred for at least 30 minutes. The organic phase was removed and MTBE (160 ml) was added to the aqueous phase prior to pH adjustment to between 9 and 11 with sodium hydroxide solution. The biphasic mixture was stirred and the separated organic phase containing Structure 8 (Gamithromycin) was washed with water (160 ml). The obtained organic phase was dried with sodium sulfate and the dried solution was concentrated to the residue. Acetonitrile was added and the mixture was concentrated back to the crude residue of Structure 8 (Gamithromycin) (6.9 g).

Example 4

Formation of Structure 8 (Gamithromycin) without Isolation of Structure 7

A compound of Structure 3 (1 g) in DMA (10 ml) with catalyst Pt/C$_5$% (0.5 g) was stirred at between 15° C. and 25° C. with a hydrogen pressure of 50 bar. Acetic acid addition (0.125 ml) was necessary to achieve reaction completion. Propanal (5 ml) and acetic acid (2.5 ml) was added to the suspension and stirred at a temperature between 40° C. and 45° C. with a hydrogen pressure of about 20 bar for at least 4 hours. Water (10 ml) was added to the suspension and the suspension was filtered through a cellulose bed. The filter cake was washed with water (10 ml) and to the resulting filtrate was added MTBE (20 ml) and the biphasic mixture was stirred for at least 30 minutes. The organic phase was removed and MTBE (20 ml) was added to the aqueous phase prior to pH adjustment to between 9 and 11 with sodium hydroxide solution. The biphasic mixture was stirred and the separated organic phase containing Structure 8 (Gamithromycin) was washed with water (20 ml). The obtained organic phase was dried with sodium sulfate and the dried solution was concentrated to the residue. Acetonitrile was added and the mixture was concentrated back to the crude residue of Structure 8 (Gamithromycin) (0.84 g).

Structure 3 was synthesized according to the current manufacturing process with a modified work-up. The process was carried out up until the heptane wash of the reaction mixture, designed to partially remove the pyridine, and the resulting oil was diluted with dichloromethane and water. The pH was then adjusted to between 9 and 10 with aqueous sodium hydroxide solution. The phases were then separated and a back wash of the aqueous phase with dichloromethane was carried out.

Isolation of Structure 3 in dichloromethane was carried out at a temperature between 0° C. to 5° C. P-Toluenesulfonic acid (hereinafter "PTSA"), from the p-toluenesulfonyl chloride reagent, remained dissolved in the aqueous phase after the phase separations.

The solvents from the combined organic phases were removed under vacuum at a temperature below 35° C. and the dichloromethane was chased with MTBE by concentrating 1 or 2 times to a residue.

The pyridine that remained in the residue was removed during crystallization from MTBE. The product was first crystallized at room temperature and then cooled to 0-5° C. and stirred at this temperature for 1 hour to increase yield.

Structure 3 was isolated after filtration and a low temperature MBTE wash of the resulting yellow cake was performed. Degradation products, Structure 5 and Structure 6, and almost all of the Structure 4 formed in the Beckmann rearrangement remained dissolved in the mother-liquors.

The yield from Structure 2 was about 65-70% by weight with a purity of the isolated Structure 3 of around 75-85% by area when utilizing HPLC. The main contaminants of Structure 3 were Structure 5 and Structure 6, each at level of 5% to 10% by area by HPLC.

Figure 3:
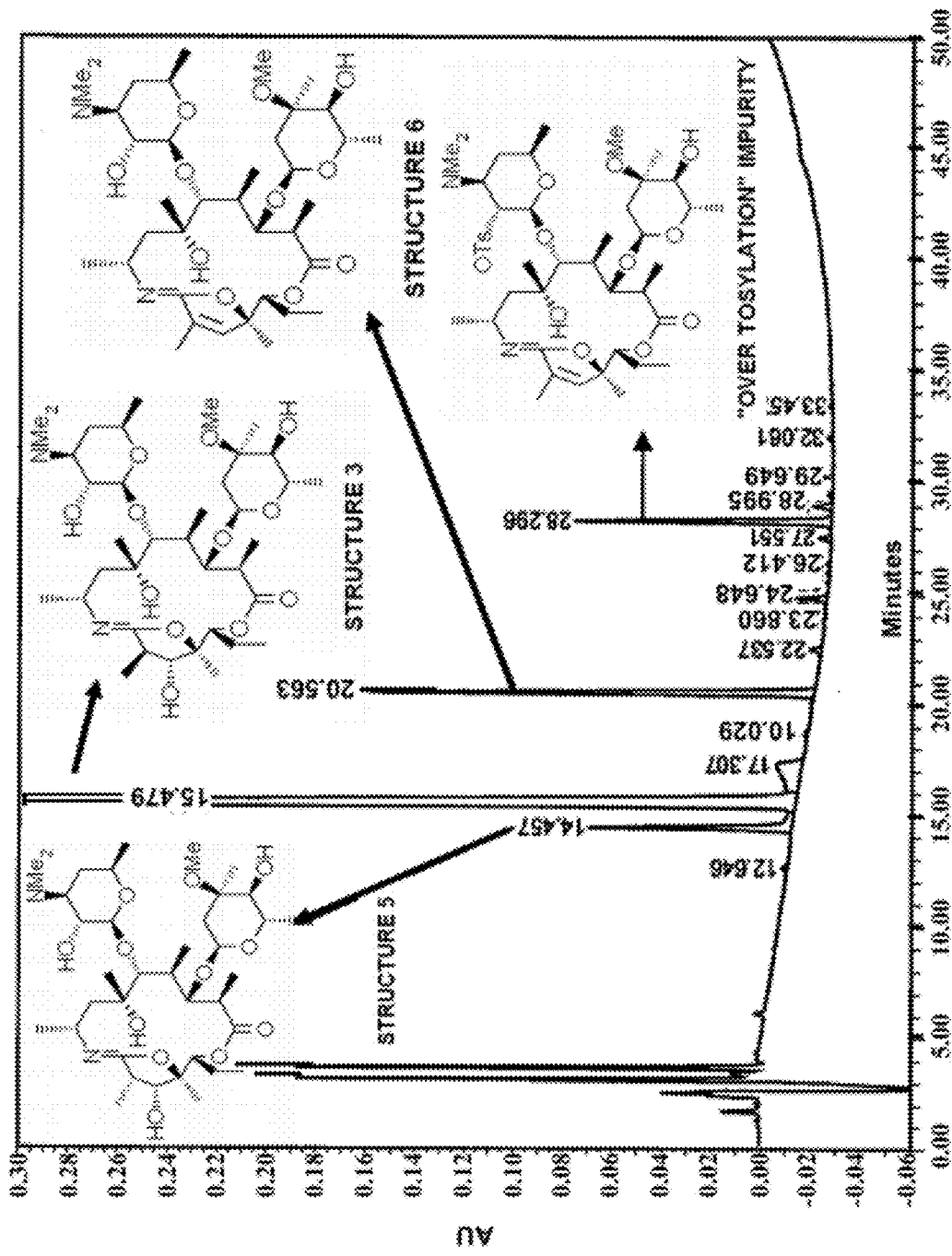
FIG. 3 depicts an HPLC trace of a sample of isolated Structure 3.

FIG. 3 depicts the HPLC trace of one batch of isolated Structure 3. The peak results for FIG. 3 are shown below in Table 1.

TABLE 1

| | RT | Name | Area | % Area |
|---|---|---|---|---|
| 1 | 12.646 | | 23039 | 0.12 |
| 2 | 14.457 | Structure 5 | 948922 | 4.82 |
| 3 | 15.479 | Structure 3 | 14663001 | 74.43 |
| 4 | 17.307 | | 625131 | 3.17 |
| 5 | 18.629 | | 8420 | 0.04 |
| 6 | 18.821 | | 9933 | 0.05 |
| 7 | 19.700 | Structure 2 | | |
| 8 | 20.563 | Structure 6 | 1935293 | 9.82 |
| 9 | 22.537 | | 52241 | 0.27 |
| 10 | 23.860 | | 5976 | 0.03 |
| 11 | 24.470 | | 6748 | 0.03 |
| 12 | 24.848 | | 120168 | 0.61 |
| 13 | 25.400 | | | |
| 14 | 25.581 | | 7889 | 0.04 |
| 15 | 25.990 | | 10197 | 0.05 |
| 16 | 26.412 | | 9086 | 0.05 |
| 17 | 27.551 | | 46974 | 0.24 |
| 18 | 28.296 | "Over Tosylation" Impurity | 1094959 | 5.56 |
| 19 | 28.995 | | 81267 | 0.41 |
| 20 | 29.549 | | 23052 | 0.12 |
| 21 | 32.061 | | 19794 | 0.10 |
| 22 | 33.457 | | 8897 | 0.05 |
| Sum | | | 19700986 | |

Although Structure 3 was unstable in solution, the solids obtained did not degrade over time, and the purity was maintained for at least 1 month.

The synthesis of Structure 7 via hydrogenation was made using a platinum oxide catalyst. The reaction mixture was stirred for about 1 day at room temperature under hydrogen at about 1000 to about 3000 psi. These conditions were the starting point for the experiments. The resulting isolated Structure 3 was used as a standard to compare products from other experiments. Other reagents/catalysts supported on carbon were also tested. Table 2 summarizes some of the results.

TABLE 2

Hydrogenation of isolated Structure 3 using several reagents/catalysts

| Solvent (quantity) | Reagent/Catalyst (quantity) | Pressure (bar) | Temperature | Purity |
|---|---|---|---|---|
| Acetic acid (40 vol.) | PtO$_2$ (100% by weight) | 50 | r.t. | Structure 7 - 64% Structure 6 - 23% |
| Acetic acid (20 vol.) | Rh/C 5% (50% by weight) | 50 | r.t. | Structure 7 - 5% Structure 6 - 63% |
| Acetic acid (40 vol.) | Pd/C 5% (50% by weight) | 50 | r.t. → 50° C. | NO Structure 7 formed |
| Acetic acid (20 vol.) | Pt/C 5% (50% by weight) | 50 | r.t. | Structure 7 - 49% Structure 6 - 38% |
| Acetic acid (40 vol.) | Pt/C 5% (66% by weight) | 50 | r.t. | Structure 7 - 29% Structure 6 - 59% |
| Acetic acid (40 vol.) | Pt/C 5% with 0.5% S (66% by weight) | 50 | r.t. | Structure 7 - 59% Structure 6 - 35% |
| Acetic acid (20 vol.) | Pt/C 5% (50% by weight) | 50 | r.t. | Structure 7 - 30% Structure 6 - 70% |
| Acetic acid (20 vol.) | Pt/C 1.5% (75% by weight) | 50 | r.t. | Structure 7 - 45% Structure 6 - 41% |
| Acetic acid (20 vol.) | Pd/C 3% (50% by weight) | 50 | r.t. | No Structure 7 formed |
| Acetic acid (20 vol.) | Pt/C 5% (50% by weight) | 50 | r.t. | Structure 7 - 31% Structure 6 - 52% |
| Acetic acid (20 vol.) | Pt/C 5% (50% by weight) | 50 | r.t. | Structure 7 - 39% Structure 6 - 45% |
| Acetic acid (20 vol.) | Pt/C 5% (50% by weight) | 50 | r.t. | Structure 7 - 50% Structure 6 - 23% |

Figure 4:
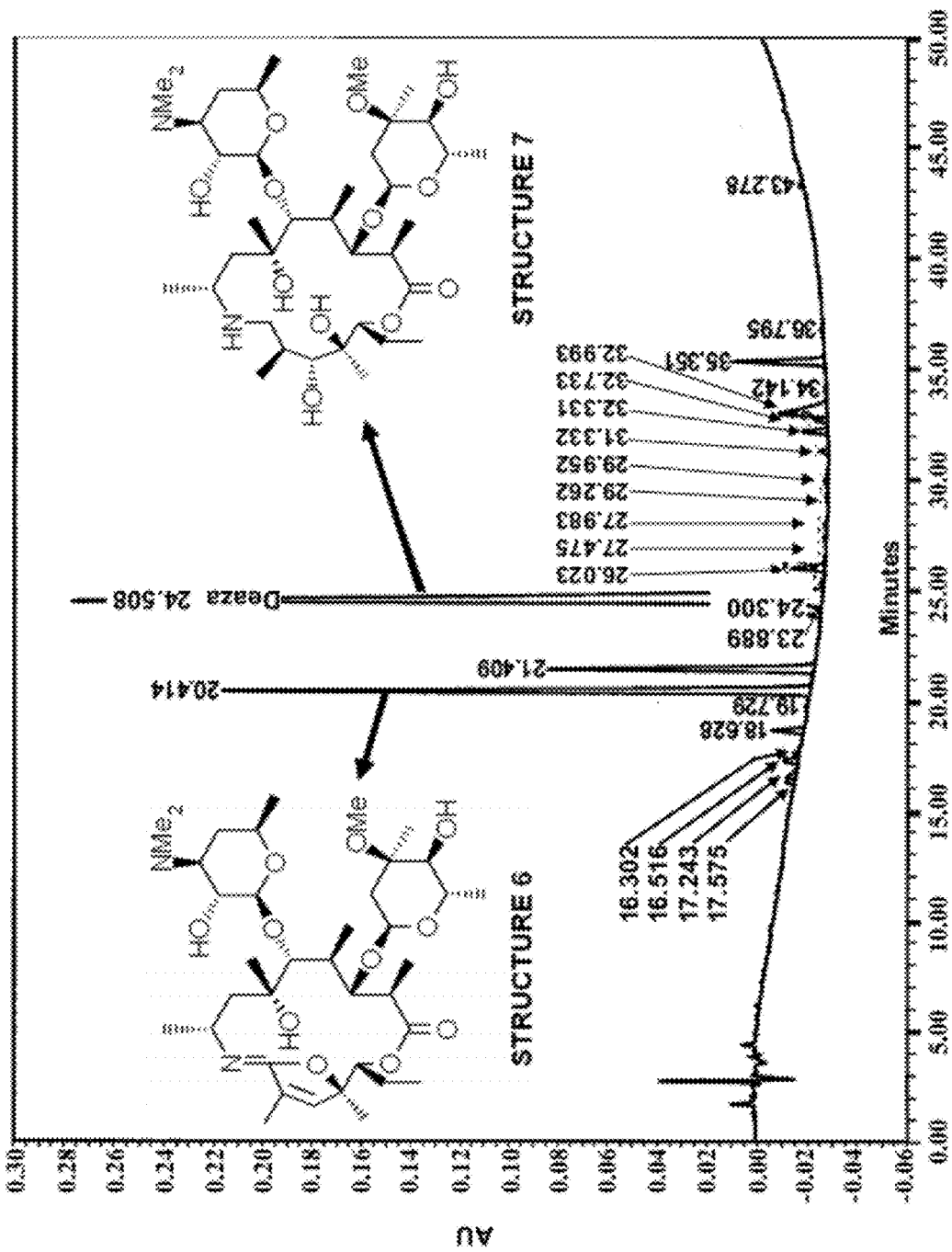
FIG. 4 depicts an HPLC trace of a sample of isolated Structure 7 obtained using hydrogenation under acidic conditions.

In the trials conducted, the catalyst Pt/C$_5$% provided a desired result for the conditions utilized. FIG. 4 presents the HPLC trace of Structure 7 obtained from a trial using the Pt/C$_5$% catalyst. The values of the area under the peak on the HPLC trace are shown in Table 3 below.

TABLE 3

|   | RT | Name | Area | % Area |
|---|---|---|---|---|
| 1 | 15.500 | Structure 3 | | |
| 2 | 16.302 | | 45449 | 0.41 |
| 3 | 16.516 | | 43684 | 0.40 |
| 4 | 17.243 | | 73435 | 0.67 |
| 5 | 17.575 | | 24360 | 0.22 |
| 6 | 18.628 | | 129219 | 1.18 |
| 7 | 19.700 | Structure 2 | | |
| 8 | 19.729 | | 11809 | 0.11 |
| 9 | 20.414 | Structure 6 | 2536368 | 23.10 |
| 10 | 21.409 | | 1189347 | 10.83 |
| 11 | 23.889 | | 47595 | 0.43 |
| 12 | 24.300 | | 28497 | 0.26 |
| 13 | 24.508 | Structure 7 | 5505606 | 50.15 |
| 14 | 25.341 | | 20326 | 0.19 |
| 15 | 26.023 | | 170383 | 1.55 |
| 16 | 26.374 | | 4586 | 0.04 |
| 17 | 27.475 | | 12623 | 0.11 |
| 18 | 27.983 | | 11830 | 0.11 |
| 19 | 29.262 | | 15805 | 0.14 |
| 20 | 29.952 | | 32113 | 0.29 |
| 21 | 31.332 | | 35383 | 0.32 |
| 22 | 32.221 | | 109461 | 1.00 |
| 23 | 32.733 | | 51617 | 0.47 |
| 24 | 32.993 | | 433397 | 3.95 |
| 25 | 34.142 | | 7096 | 0.06 |
| 26 | 35.351 | | 406681 | 3.70 |
| 27 | 36.795 | | 10093 | 0.09 |
| 28 | 43.278 | | 22005 | 0.20 |
| Sum | | | 10978866 | |

The use of platinum oxide also gave a desired result.

The standard conditions used to carry out the hydrogenation were: 20 volumes of acetic acid; room temperature; 50 bar hydrogen; and an overnight stir were used in almost all of the laboratory trials. From the survey of catalysts platinum appeared to be the ideal noble metal for this reaction.

All of the tests in this initial study gave Structure 7 with a considerable amount of Structure 6. Stability data showed that when a solution of Structure 3 when stirred with 20 volumes of acetic acid at room temperature, Structure 3 was completely degraded to Structure 5 and Structure 6 after a few hours. Since these conditions were used in the hydrogenation, it was concluded that degradation of Structure 3 due to the acidic conditions was competing with the formation of Structure 7.

Hence, the reaction was tried in DMEU instead of acetic acid. The results were surprising, the reaction was cleaner with only a small amount of Structure 6 formed and the reaction rate was similar to the reactions carried out using acetic acid as a solvent.

Other solvents with characteristics similar to the DMEU, such as DMF and DMA were then tested. Tests showed that Structure 3 was unchanged in a solution of DMEU, DMF or DMA at a temperature of about 5° C. for 3-4 hours, and with only a small amount of degradation at room temperature after 1 day of stirring.

Table 4 summarizes the results of the hydrogenations carried out using these solvents and the conditions.

TABLE 4

Hydrogenation of isolated Structure 3 using DMEU, DMF and DMA

| Solvent (quantity) | Reagent/Catalyst (quantity) | Pressure (bar) | Temperature | Purity |
|---|---|---|---|---|
| DMEU (20 vol.) | Pt/C 5% (50% BY WEIGHT) | 50 | 5° C. → r.t. | Structure 7 - 90% Structure 6 - 1.4% |
| DMF (20 vol.) | Pt/C 5% (50% BY WEIGHT) | 50 | 5-10° C. | Structure 7 - 85% Structure 6 - 3.8% |
| DMA (20 vol.) | Pt/C 5% (50% BY WEIGHT) | 50 | 5-10° C. | Structure 7 - 86.5% Structure 6 - 1.6% |
| DMA (10 vol.) | Pt/C 5% (25% BY WEIGHT) | 50 | 5-20° C. | Structure 7 - 87% Structure 6 - 3.5% |
| DMA (10 vol.) | Pt/C 5% (50% BY WEIGHT) | 50 | 15-20° C. | Structure 7 - 87% Structure 6 - 1.4% |

The hydrogenations were carried out at a temperature between 5° C. and 20° C. In some reactions, acetic acid (0.25-0.5 volumes) was added toward the end of the reaction. The total solvent volume was reduced from 20 volumes to 10 volumes while a reduction in the quantity of the platinum catalyst was made without affecting the reaction performance significantly.

DMA was the solvent chosen. The work-up was as follows:

The reaction mixture was passed through a cellulose filter. The reactor was rinsed with water. The rinsed water was used to wash the cellulose plug. Dichloromethane was added to the filtrate and the pH of the mixture was adjusted to between 4.5 and 5.5 with acetic acid, if necessary, before phase separation. Dichloromethane was added to the aqueous phase and the pH was adjusted to between 9 and 11 with aqueous sodium hydroxide solution. The resulting organic phase containing the product was washed with water to remove some DMA still present and then concentrated to afford a white foam.

Figure 5:
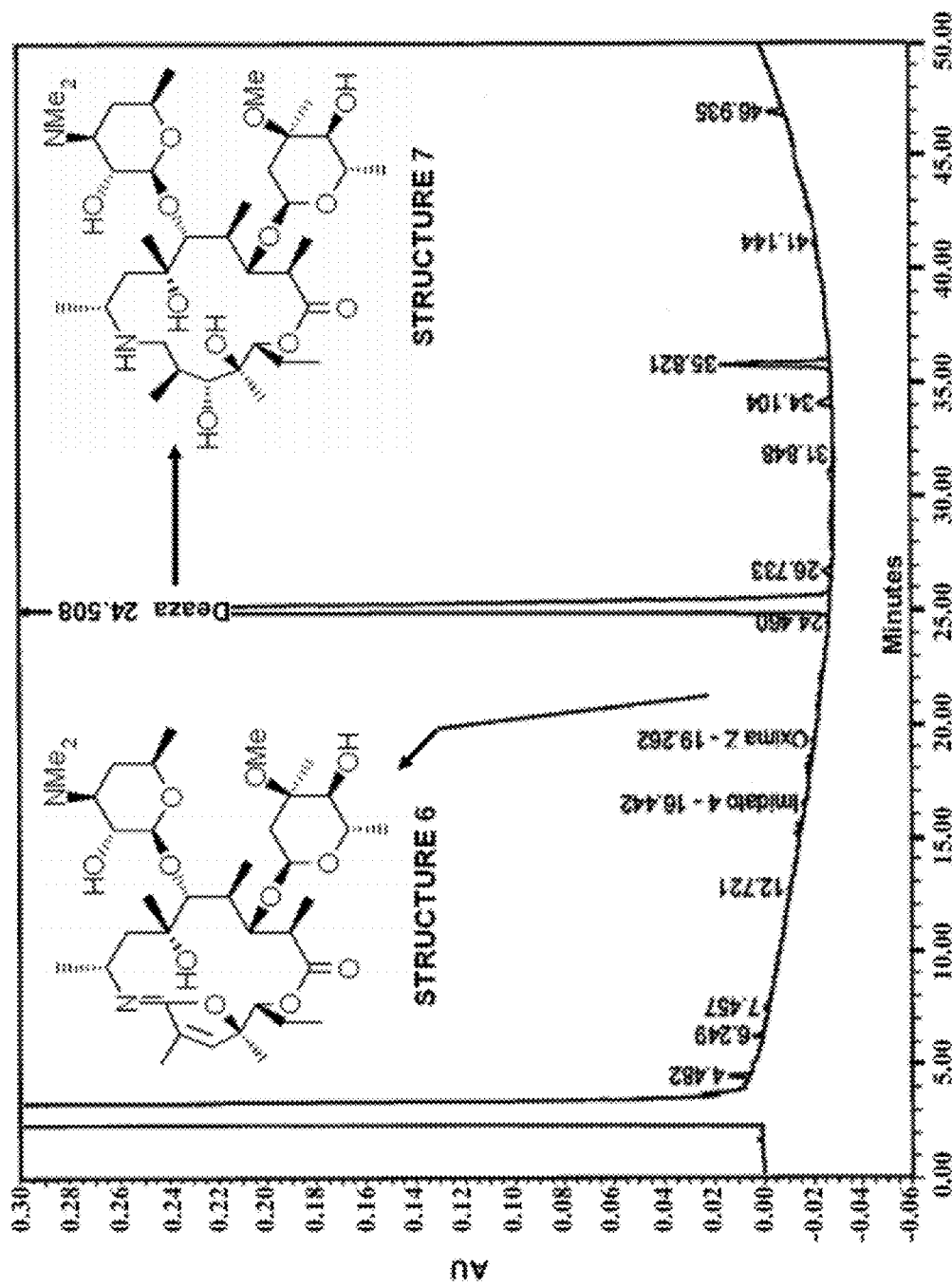
FIG. 5 depicts an HPLC trace of a sample of isolated Structure 7 obtained using hydrogenation under less acidic conditions.

FIG. 5 depicts the HPLC trace of Structure 7 obtained from another laboratory trial utilizing 10 volumes of DMA and the platinum catalyst. The values of the area under the peak on the HPLC trace are shown in Table 5 below.

TABLE 5

| | RT | RRT | Name | Area | % Area |
|---|---|---|---|---|---|
| 1 | 4.482 | 0.233 | | 60529 | 0.58 |
| 2 | 6.249 | 0.324 | | 29113 | 0.28 |
| 3 | 7.457 | 0.387 | | 26836 | 0.26 |
| 4 | 12.721 | 0.660 | | 6900 | 0.07 |
| 5 | 15.188 | 0.789 | | 18851 | 0.18 |
| 6 | 15.513 | 0.805 | | 16914 | 0.16 |
| 7 | 16.442 | 0.854 | Structure 3 | 10800 | 0.10 |
| 8 | 17.827 | 0.926 | | 12612 | 0.12 |
| 9 | 18.129 | 0.941 | | 30191 | 0.29 |
| 10 | 18.503 | 0.961 | | 11329 | 0.11 |
| 11 | 19.262 | 1.000 | Structure 2 | 7558 | 0.07 |
| 12 | 20.725 | 1.076 | | 8729 | 0.08 |
| 13 | 21.093 | 1.095 | Structure 6 | 142158 | 1.36 |
| 14 | 21.800 | 1.132 | | 4515 | 0.04 |
| 15 | 22.080 | 1.146 | | 34763 | 0.33 |
| 16 | 24.460 | 1.270 | | 7392 | 0.07 |
| 17 | 25.010 | 1.298 | Structure 7 | 9089710 | 86.99 |
| 18 | 26.733 | 1.388 | | 49639 | 0.48 |
| 19 | 28.061 | 1.457 | | 16743 | 0.16 |
| 20 | 28.565 | 1.483 | | 14803 | 0.14 |
| 21 | 28.880 | 1.499 | | 26345 | 0.25 |
| 22 | 29.673 | 1.541 | | 12139 | 0.12 |
| 23 | 29.883 | 1.551 | | 1998 | 0.02 |
| 24 | 30.942 | 1.606 | | 47982 | 0.46 |
| 25 | 31.848 | 1.653 | | 2627 | 0.03 |
| 26 | 34.104 | 1.771 | | 88091 | 0.84 |

TABLE 5-continued

| | RT | RRT | Name | Area | % Area |
|---|---|---|---|---|---|
| 27 | 35.821 | 1.860 | | 512336 | 4.90 |
| 28 | 41.144 | 2.136 | | 19501 | 0.19 |
| 29 | 42.567 | 2.210 | | 3945 | 0.04 |
| 30 | 42.929 | 2.229 | | 62709 | 0.60 |
| 31 | 46.935 | 2.437 | | 71390 | 0.68 |
| Sum | | | | 1044918 | |

An attempt was made to synthesize Structure 7 directly from the Z-oxime. The same work-up procedure as described above was applied but instead of isolating the Structure 3 by addition of MTBE, 10 volumes of DMA and 50% by weight of $Pt/C_5\%$ catalyst were added. The resulting mixture was stirred at a temperature of about 15° C. under 50 bar hydrogen pressure. The reaction proceeded as expected but an oil was obtained with a mixture of Structure 7 with about 40% by area by HPLC together with Structure 4 with about 42% by area by HPLC.

Since Structure 4 was not removed by crystallization and Structure 3 was not isolated, it was carried through to the isolated Structure 7. The presence of Structure 4 in the hydrogenation may have had an influence on the impurity profile obtained, although it seemed to be inert in the hydrogenation conditions. Residual pyridine, which was not removed because Structure 3 was not isolated, also influenced the quality of the Structure 7 obtained.

Structure 8 (Gamithromycin) was prepared by carrying out a reductive amination of Structure 7 in the presence of propanal. This reaction was carried out under catalytic conditions using hydrogen and a palladium catalyst. Several palladium catalysts and a smaller amount of platinum catalysts were screened in this transformation. With about 10 equivalents of propanal in ethanol the reactions were slow and incomplete. Using propanal in a large excess allowed for a complete reaction within a few hours. The propanal acted as both reagent and solvent.

Attempts using an acetate buffer solution to achieve a pH of 5.0 to 5.5 were made. However, it was subsequently established that the pH of the reaction mixture needs only to be set to between 5.0 and 5.5 with acetic acid before hydrogenation.

Table 6 summarizes some of the results and conditions for the synthesis of Structure 8 (Gamithromycin).

TABLE 6

Results and conditions of the reductive amination of Structure 7

| Solvent (quantity) | Reagent/Catalyst (quantity) | Pressure (bar) | Initial pH | Temperature | Purity |
|---|---|---|---|---|---|
| Propanal (10 vol.) | Pd/C 5% (100% by weight) | 20 | 4.70 | 40-45° C. | Structure 8 (Gamithromycin) - 42% |
| Propanal (10 vol.) | Pd/C 3% (100% by weight) | 20 | 5.23 | 40-45° C. | Structure 8 (Gamithromycin) - 96% |
| Propanal (10 vol.) | Pt/C 5% with 0.5% S (50% by weight) | 10 | 5.06 | 40-45° C. | Structure 8 (Gamithromycin) - 46% Structure 7 - 12% |
| Propanal (20 vol.) | Pt/C 5% (100% by weight) | 20 | — | 40-45° C. | Structure 8 (Gamithromycin) - 88% |
| Propanal (10 vol.) | Pd/C 3% (100% by weight) | 20 | 5.49 | 40-45° C. | Structure 8 (Gamithromycin) - 89% |

Initial tests indicated that hydrogenation at room temperature had a slow rate of reaction. As a result, a temperature range of 40-45° C. was used for almost all reactions. The pH of the reaction mixture fell to a range of about 4.0 to about 4.5 during the hydrogenation.

Figure 6:
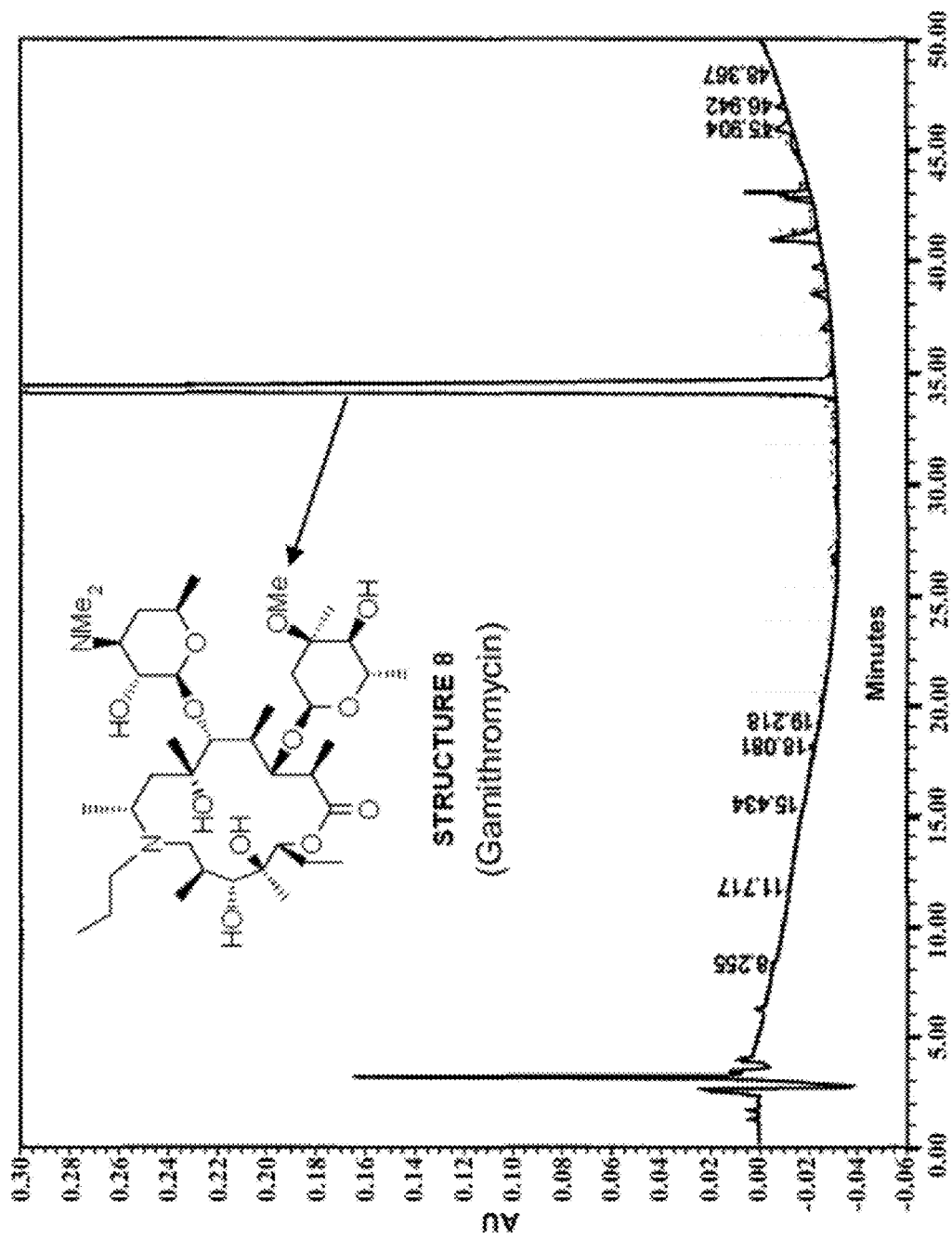
FIG. 6 depicts an HPLC trace of a sample of Structure 8 (Gamithromycin).

Structure 8 (Gamithromycin) was obtained after work-up as described above but using MTBE as the extracting solvent. The yields depended significantly on the quality of the Structure 7 synthesized and on the scale of the laboratory experiment. Structure 8 (Gamithromycin) was obtained with a yield of 86% by weight from 8 g of isolated Structure 3. FIG. 6 depicts the HPLC trace of a typical isolated Structure 8 (Gamithromycin). The values of the area under the peak on the HPLC trace are shown in Table 7 below.

TABLE 7

| | RT | RRT | Name | Area | % Area |
|---|---|---|---|---|---|
| 1 | 8.255 | 0.242 | | 7309 | 0.05 |
| 2 | 11.717 | 0.343 | | 3245 | 0.02 |
| 3 | 15.434 | 0.452 | | 2903 | 0.02 |
| 4 | 18.081 | 0.529 | | 16167 | 0.11 |
| 5 | 19.218 | 0.562 | | 4256 | 0.03 |
| 6 | 20.235 | 0.592 | | 11132 | 0.07 |
| 7 | 21.027 | 0.615 | | 1696 | 0.01 |
| 8 | 22.003 | 0.644 | | 1388 | 0.01 |
| 9 | 22.797 | 0.667 | | 1366 | 0.01 |
| 10 | 23.200 | 0.679 | | 2027 | 0.01 |
| 11 | 23.938 | 0.700 | | 2338 | 0.02 |
| 12 | 24.327 | 0.712 | | 23838 | 0.16 |
| 13 | 24.725 | 0.723 | | 4942 | 0.03 |
| 14 | 25.457 | 0.745 | | 3033 | 0.02 |
| 15 | 26.469 | 0.774 | | 20898 | 0.14 |
| 16 | 26.753 | 0.783 | | 40372 | 0.27 |
| 17 | 27.407 | 0.802 | | 10260 | 0.07 |
| 18 | 28.108 | 0.822 | | 4246 | 0.03 |
| 19 | 28.420 | 0.832 | | 1291 | 0.01 |
| 20 | 29.200 | 0.854 | | 11826 | 0.08 |
| 21 | 29.310 | 0.858 | | 29056 | 0.19 |
| 22 | 29.847 | 0.873 | | 15468 | 0.10 |
| 23 | 30.303 | 0.887 | | 4789 | 0.03 |
| 24 | 30.767 | 0.900 | | 7826 | 0.05 |
| 25 | 31.215 | 0.913 | | 10291 | 0.07 |
| 26 | 31.717 | 0.928 | | 813 | 0.01 |
| 27 | 31.931 | 0.934 | | 18022 | 0.12 |
| 28 | 32.319 | 0.946 | | 2588 | 0.02 |
| 29 | 32.590 | 0.954 | | 8105 | 0.05 |
| 30 | 33.093 | 0.968 | | 70110 | 0.47 |
| 31 | 33.504 | 0.980 | | 1750 | 0.01 |
| 32 | 34.176 | 1.000 | Structure 8 | 13341092 | 88.88 |
| 33 | 35.049 | 1.026 | | 21138 | 0.14 |
| 34 | 35.614 | 1.042 | | 13337 | 0.09 |
| 35 | 36.615 | 1.071 | | 457 | 0.00 |
| 36 | 37.041 | 1.084 | | 57533 | 0.38 |
| 37 | 38.514 | 1.127 | | 92101 | 0.61 |
| 38 | 39.107 | 1.144 | | 8684 | 0.06 |
| 39 | 39.687 | 1.161 | | 63300 | 0.42 |
| 40 | 40.935 | 1.198 | | 400243 | 2.67 |
| 41 | 41.533 | 1.215 | | 3963 | 0.03 |
| 42 | 41.750 | 1.222 | | 3210 | 0.02 |
| 43 | 42.100 | 1.232 | | 807 | 0.01 |
| 44 | 42.794 | 1.252 | | 116557 | 0.78 |
| 45 | 43.002 | 1.258 | | 242434 | 1.62 |
| 46 | 43.283 | 1.266 | | 6321 | 0.04 |
| 47 | 45.183 | 1.322 | | 103524 | 0.69 |
| 48 | 45.904 | 1.343 | | 150603 | 1.00 |
| 49 | 46.942 | 1.374 | | 37328 | 0.25 |
| 50 | 48.367 | 1.415 | | 4688 | 0.03 |
| Sum | | | | 15010670 | |

Since the reductive amination was carried out using a platinum catalyst, it was possible to test the use of the same platinum catalyst for the synthesis of Structure 8 (Gamithromycin) from Structure 3 without isolating Structure 7.

In one laboratory trial Structure 7 was synthesized from isolated Structure 3 using 10 volumes of DMA as a solvent and 50% by weight of Pt/C$_5$% as described above. After complete reaction to form Structure 7, which was not isolated, 5 volumes of propanal were added and the pH was adjusted to about 5.4 with acetic acid and hydrogenation was carried out as before in the conditions described above.

Structure 7 was converted into Structure 8 (Gamithromycin), the residual DMA had no detrimental affect. Both hydrogenation reactions proceeded, as expected, with similar conversion rates to reactions starting from isolated intermediates.

After the work-up as described above, Structure 8 (Gamithromycin) was obtained with a yield of 84% by weight from Structure 3. Although the yield was comparable with the laboratory trial where Structure 7 was isolated, the purity was lower (78% by area when measured utilizing HPLC).

Figure 7:
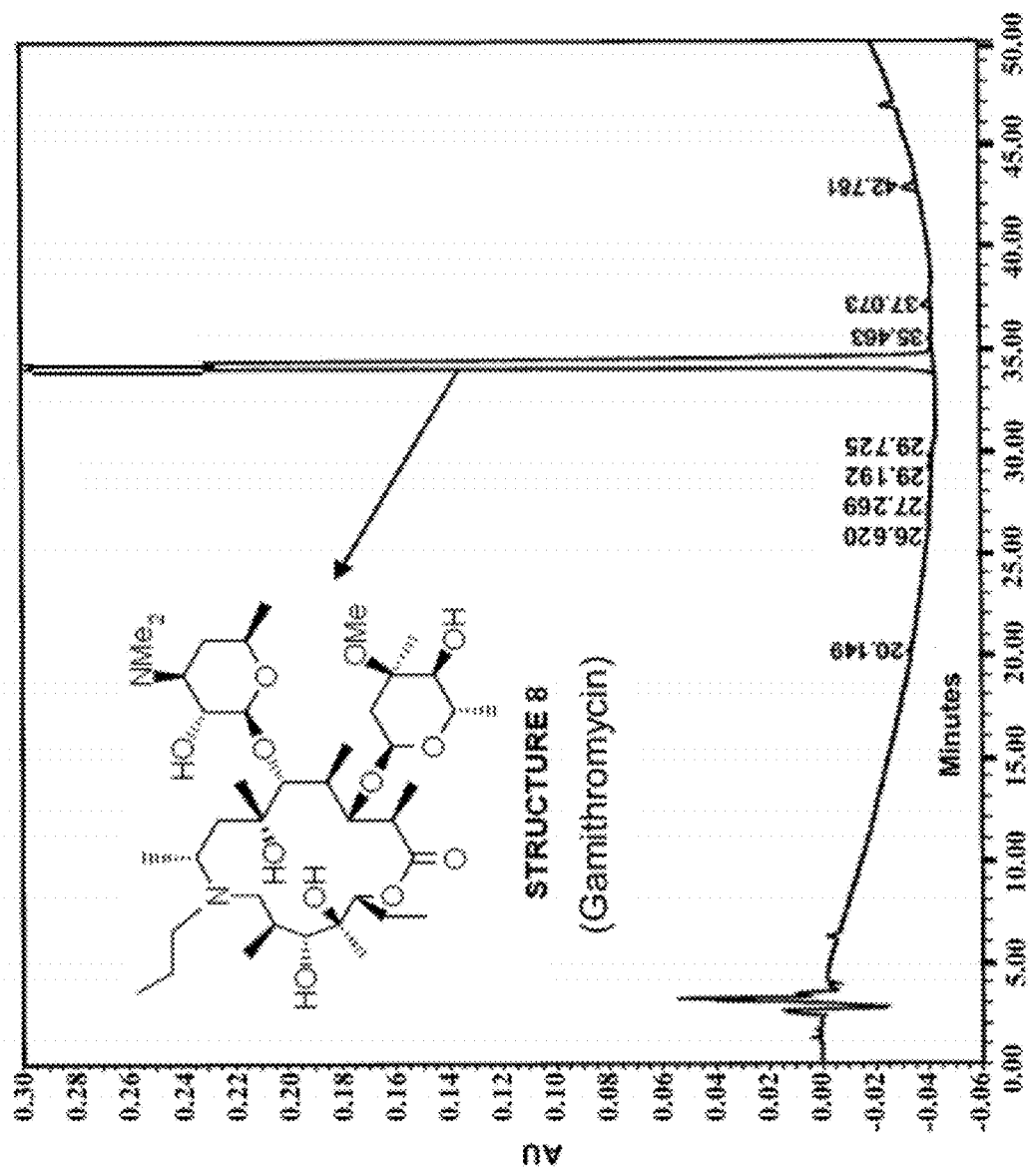
FIG. 7 depicts an HPLC trace of a sample of isolated gamithromycin.

Several laboratory batches of Structure 8 (gamithromycin) were crystallized to form isolated gamithromycin (Structure 8) having a yield of about 70-80% by weight and a purity usually above 98% by area when measured utilizing HPLC. FIG. 7 depicts the HPLC trace of one of those batches of Structure 8 (Gamithromycin). The values of the area under the peak on the HPLC trace are shown in Table 8 below.

TABLE 8

| | RT | RRT | Name | Area | % Area |
|---|---|---|---|---|---|
| 1 | 20.149 | 0.591 | | 16944 | 0.14 |
| 2 | 26.620 | 0.780 | | 6928 | 0.06 |
| 3 | 27.269 | 0.799 | | 2124 | 0.02 |
| 4 | 29.192 | 0.856 | | 21806 | 0.18 |
| 5 | 29.723 | 0.871 | | 19650 | 0.17 |
| 6 | 34.108 | 1.000 | Structure 8 | 11629284 | 98.19 |
| 7 | 35.463 | 1.040 | | 10530 | 0.09 |
| 8 | 37.073 | 1.087 | | 46419 | 0.39 |
| 9 | 42.781 | 1.254 | | 89503 | 0.76 |
| Sum | | | | 11843187 | |

Figure 8:
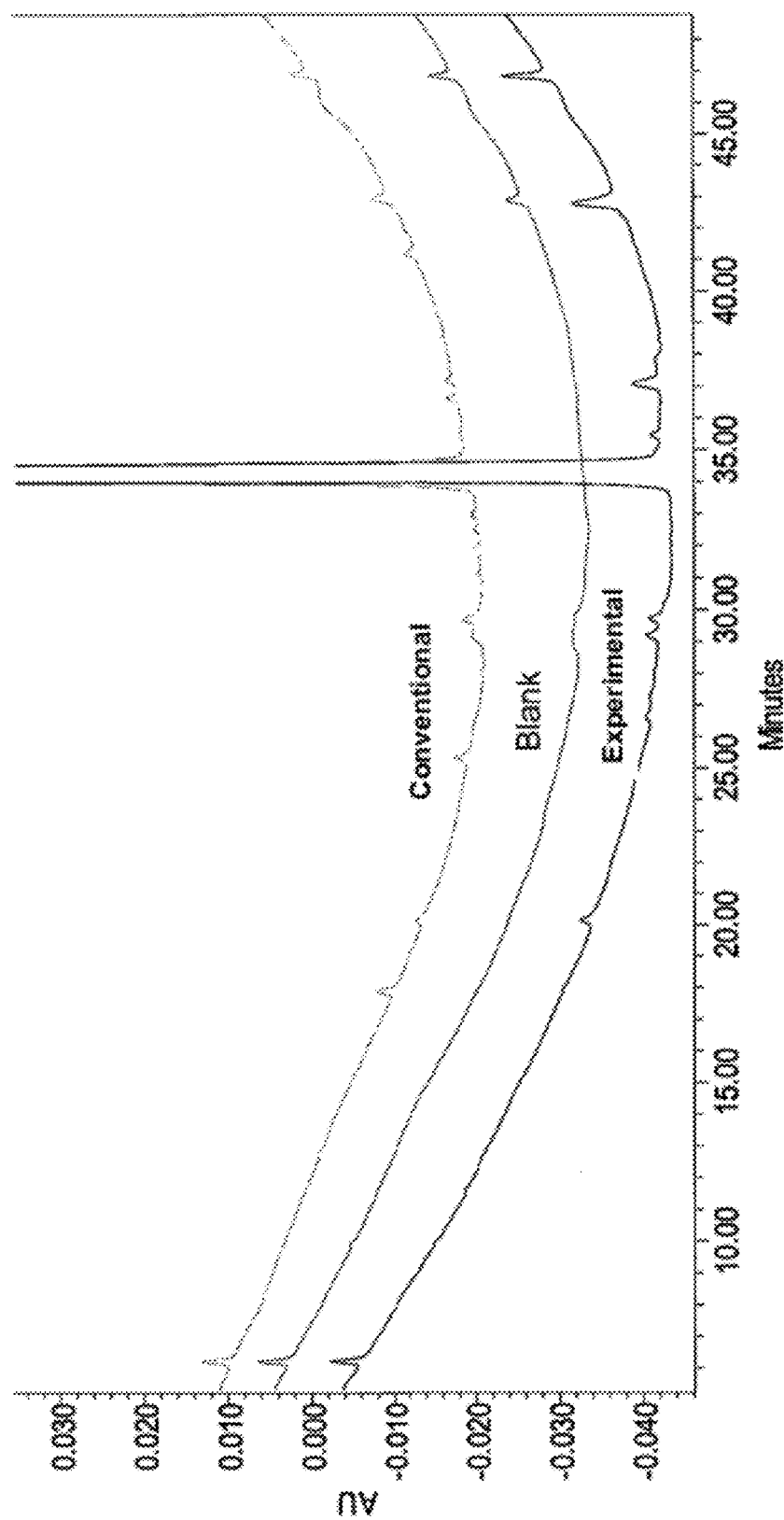
FIG. 8 depicts an overlay of an HPLC trace of a convention synthesis method and an HPLC trace of the method described herein.

In FIG. 8 this HPLC trace was overlaid with a Structure 8 (Gamithromycin) trace from conventional production. From a comparison of the two HPLC profiles, the formation of new impurities was not observed. Hence, this new process can be applied giving Structure 8 (Gamithromycin) with a similar impurity profile to that of the current manufacturing process.

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:

1. A process for synthesizing a macrolide compound comprising:
   (i) converting a compound of structure 2 to a compound of structure 3;

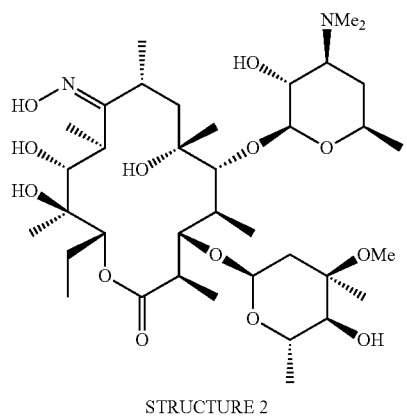

STRUCTURE 2

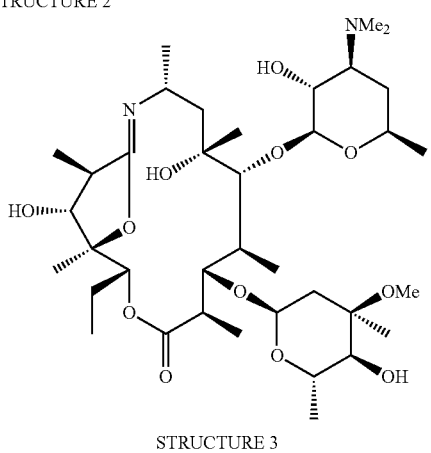

STRUCTURE 3

(ii) reducing the compound of structure 3 with hydrogen in the presence of
   a) a platinum or palladium catalyst;
   b) a polar aprotic solvent, selected from N,N'-dimethylethyleneurea, dimethylacetamide, dimethylformamide and combinations thereof;
(iii) adding acetic acid toward the end of the reaction to achieve reaction completion; and

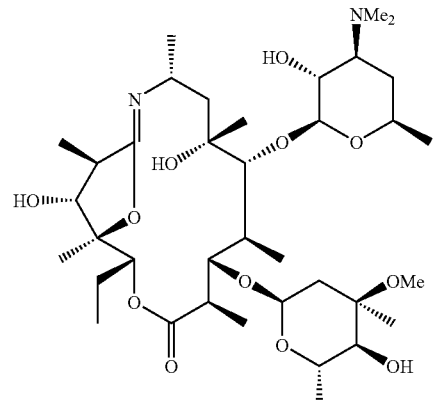

STRUCTURE 3

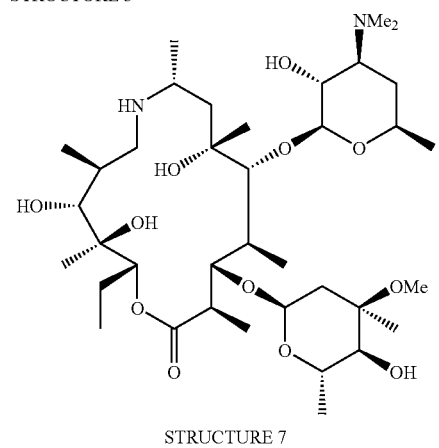

STRUCTURE 7

(iv) reacting the compound of structure 7 with an aldehyde of structure R—C(O)H in the presence of a reducing agent to form a compound of Structure 8a;
wherein R is hydrogen, alkyl, alkenyl, alkynyl, aryl, heteroaryl, or aralkyl

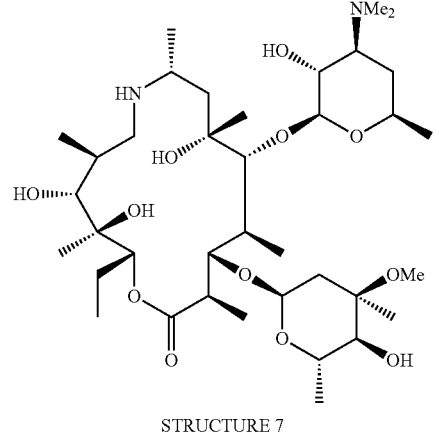

STRUCTURE 7

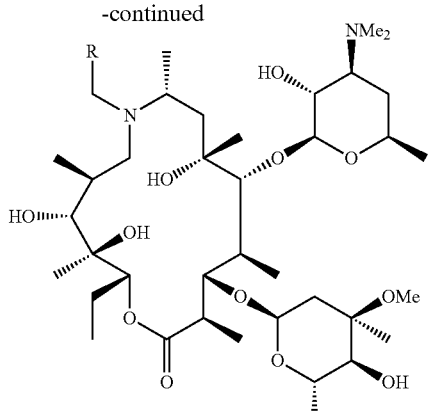

STRUCTURE 8a

2. The process of claim 1, wherein in step i) the compound of Structure 2 is treated with a sulfonylating agent to convert the compound of Structure 2 to the compound of Structure 3.

3. The process of claim 2, wherein the sulfonylating agent is p-toluenesulfonyl chloride.

4. The process of claim 1, wherein the compound of Structure 3 in step (i) is isolated prior to step (ii).

5. The process of claim 4, wherein the compound of Structure 3 is isolated at a temperature of about −20° C. to about 10° C.

6. The process of claim 1, wherein the step ii) is carried out in the presence of a platinum, catalyst.

7. The process of claim 1, wherein the polar aprotic solvent in step ii) is N,N'-dimethylethyleneurea or dimethylacetamide.

8. The process of claim 7, wherein the polar aprotic solvent is dimethylacetamide.

9. The process of claim 4, wherein the compound of Structure 3 is isolated at a temperature of below about 10° C.

10. The process of claim 1, wherein steps (iii) and (iv) are conducted without isolating the compound of Structure 7.

11. The process of claim 1 or 10, wherein in step (iv) RC(O)H is propanal and the compound of Structure 8a is gamithromycin of Structure 8:

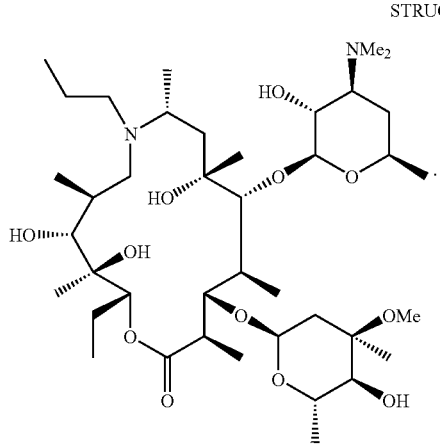

STRUCTURE 8

12. The process of claim 1, wherein the compound of Structure 3 in step (i) is not isolated prior to step (ii).

13. The process of claim 1 wherein the compound of Structure 7 is isolated prior to step (iv).

14. A process according to claim 1 for synthesizing the macrolide compound, which is gamithromycin, comprising:

(i) converting a compound of structure 2 to a compound of structure 3;

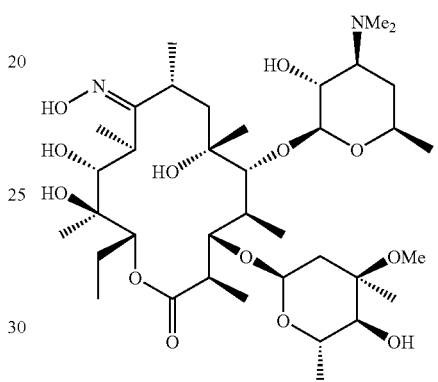

STRUCTURE 2

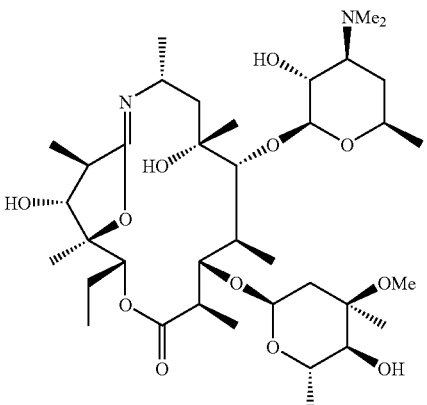

STRUCTURE 3

(ii) reducing the compound of structure 3 with hydrogen in the presence of a) a platinum or palladium catalyst;

b) a polar aprotic solvent, selected from N,N'-dimethylethyleneurea, dimethylacetamide, dimethylformamide and combinations thereof;

(iii) adding acetic acid toward the end of the reaction to achieve reaction completion; and

27

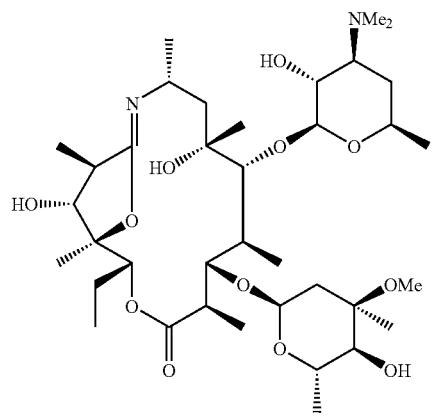

STRUCTURE 3

→

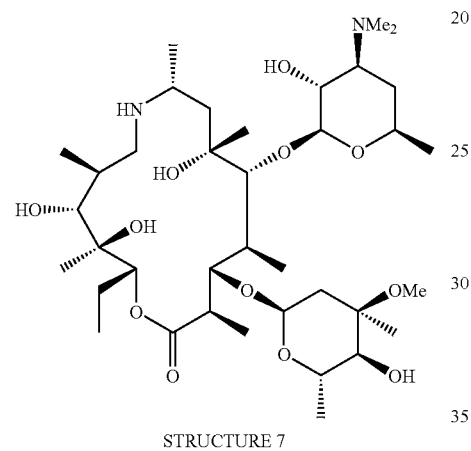

STRUCTURE 7

(iv) reacting the compound of structure 7 with propanal in the presence of a reducing agent to form gamithromycin of Structure 8; and

28 wherein the compound of structure 7 from step (ii) or (iii) is not isolated prior to step (iv)

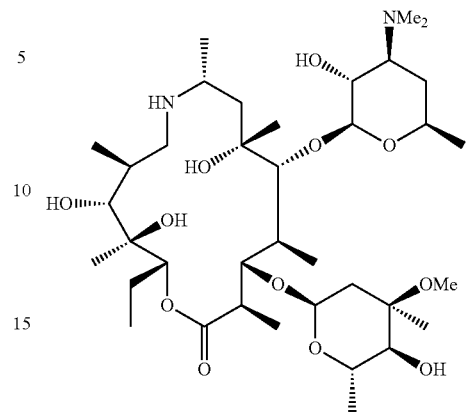

STRUCTURE 7

→

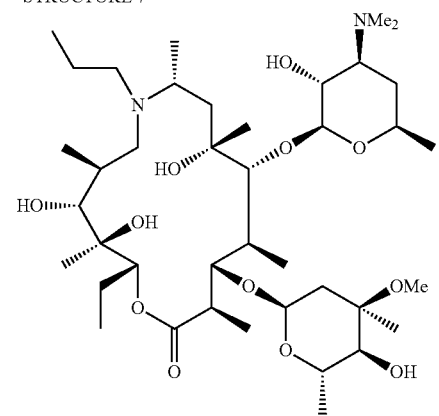

STRUCTURE 8

15. The process of claim 14, wherein the polar aprotic solvent in step (ii) is N,N'-dimethylethyleneurea, dimethylacetamide, or mixtures thereof.

\* \* \* \* \*